(12) United States Patent
Zhang et al.

(10) Patent No.: US 11,382,522 B2
(45) Date of Patent: Jul. 12, 2022

(54) POSITION DETECTION OF BLOOD PRESSURE DEVICE

(71) Applicant: Fitbit, Inc., San Francisco, CA (US)

(72) Inventors: Xi Zhang, San Francisco, CA (US); Keith Adam Wong, San Francisco, CA (US); Andrew Larsen Axley, Mountain View, CA (US); Dan Stefan Tudose, Bucharest (RO); Conor Joseph Heneghan, Campbell, CA (US)

(73) Assignee: Fitbit, Inc., San Francisco, CA (US)

( * ) Notice: Subject to any disclaimer, the term of this patent is extended or adjusted under 35 U.S.C. 154(b) by 217 days.

(21) Appl. No.: 15/855,988

(22) Filed: Dec. 27, 2017

(65) Prior Publication Data

US 2019/0099095 A1    Apr. 4, 2019

Related U.S. Application Data

(63) Continuation of application No. 15/855,932, filed on Dec. 27, 2017.
(Continued)

(51) Int. Cl.
*A61B 5/022* (2006.01)
*A61B 5/00* (2006.01)
(Continued)

(52) U.S. Cl.
CPC ........ *A61B 5/02241* (2013.01); *A61B 5/6826* (2013.01); *A61B 5/7278* (2013.01);
(Continued)

(58) Field of Classification Search
None
See application file for complete search history.

(56) References Cited

U.S. PATENT DOCUMENTS

| 3,482,565 A | 12/1969 | Gowen |
| 4,958,636 A | 9/1990 | Blandino |

(Continued)

FOREIGN PATENT DOCUMENTS

| KR | 10-0659162 | 12/2006 |
| KR | 10-2010-0042566 | 4/2010 |

(Continued)

OTHER PUBLICATIONS

International Search Report and Written Opinion—PCT/US18/052892—ISA/KR—dated Jan. 11, 2019 (Nov. 1, 2019).

(Continued)

*Primary Examiner* — Alex M Valvis
*Assistant Examiner* — Aurelie H Tu
(74) *Attorney, Agent, or Firm* — Dority & Manning, P.A.

(57) ABSTRACT

An aspect of the disclosure pertains to detecting a position of a blood pressure measurement device. An inflatable bladder of the blood pressure measurement device defines, at least in part, a pressurizable volume. The inflatable bladder may be inflated to pressurize a user's appendage and temporarily occlude blood flow in the user's appendage. A pump may initiate inflation of the inflatable bladder when one or more accelerometers and/or one or more proximity sensors determine that the blood pressure measurement device is within sufficient proximity or elevation to a user's heart and stationary.

15 Claims, 17 Drawing Sheets

Related U.S. Application Data

(60) Provisional application No. 62/566,202, filed on Sep. 29, 2017.

(51) Int. Cl.
*A61B 5/021* (2006.01)
*A61B 5/11* (2006.01)

(52) U.S. Cl.
CPC ....... *A61B 5/02116* (2013.01); *A61B 5/02225* (2013.01); *A61B 5/1121* (2013.01)

(56) References Cited

U.S. PATENT DOCUMENTS

| | | | |
|---|---|---|---|
| 4,969,466 A | 11/1990 | Brooks | |
| 4,974,599 A * | 12/1990 | Suzuki | A61B 5/0404 600/509 |
| 5,111,539 A | 8/1992 | Hiruta et al. | |
| 5,423,322 A | 6/1995 | Clark et al. | |
| 5,778,879 A * | 7/1998 | Ota | A61B 5/022 600/310 |
| 6,099,476 A | 8/2000 | Engel | |
| 6,450,966 B1 | 9/2002 | Hanna | |
| 10,874,308 B2 | 12/2020 | Zhang et al. | |
| 2002/0072681 A1 | 6/2002 | Schnali | |
| 2005/0096552 A1 | 5/2005 | Law et al. | |
| 2005/0171445 A1* | 8/2005 | Millay | A61B 5/02 600/499 |
| 2005/0215912 A1* | 9/2005 | Freund | A61B 5/022 600/485 |
| 2007/0021672 A1* | 1/2007 | Lee | A61B 5/02241 600/499 |
| 2007/0055163 A1* | 3/2007 | Asada | A61B 5/02225 600/485 |
| 2007/0106359 A1 | 5/2007 | Schaer et al. | |
| 2007/0123784 A1 | 5/2007 | Hersh et al. | |
| 2007/0135720 A1 | 6/2007 | Vinocur | |
| 2007/0142730 A1 | 6/2007 | Laermer et al. | |
| 2007/0185401 A1 | 8/2007 | Quinn et al. | |
| 2008/0243009 A1 | 10/2008 | Hersh et al. | |
| 2009/0118628 A1 | 5/2009 | Zhou et al. | |
| 2010/0049059 A1* | 2/2010 | Ha | A61B 5/021 600/485 |
| 2010/0168565 A1* | 7/2010 | Lading | A61B 5/0002 600/437 |
| 2011/0009756 A1 | 1/2011 | Meriläinen | |
| 2011/0054329 A1* | 3/2011 | Katsumoto | A61B 5/021 600/490 |
| 2011/0105917 A1 | 5/2011 | Fortin et al. | |
| 2011/0152650 A1 | 6/2011 | Donehoo et al. | |
| 2011/0160597 A1* | 6/2011 | Lane | A61B 5/02225 600/493 |
| 2012/0215082 A1* | 8/2012 | Chen | A61B 5/022 600/335 |
| 2013/0035569 A1 | 2/2013 | Heanue et al. | |
| 2013/0211269 A1 | 8/2013 | Leschinsky | |
| 2013/0226015 A1 | 8/2013 | Lam et al. | |
| 2013/0237865 A1* | 9/2013 | Sato | A61B 5/1072 600/499 |
| 2014/0257050 A1* | 9/2014 | Kuroda | A61B 5/0205 600/301 |
| 2014/0257116 A1 | 9/2014 | Kobayashi et al. | |
| 2015/0045679 A1 | 2/2015 | St. Pierre et al. | |
| 2015/0094602 A1 | 4/2015 | Yamashita et al. | |
| 2015/0133742 A1* | 5/2015 | Lane | A61B 5/021 600/301 |
| 2015/0220109 A1 | 8/2015 | von Badinski et al. | |
| 2015/0366464 A1* | 12/2015 | Gu | A61B 5/489 600/485 |
| 2016/0029900 A1* | 2/2016 | LaPlante | A61B 5/7282 600/490 |
| 2016/0029904 A1* | 2/2016 | Quinn | A61B 5/0024 600/499 |
| 2017/0000355 A1 | 1/2017 | Lenehan et al. | |
| 2017/0125749 A1 | 5/2017 | Takahagi et al. | |
| 2017/0245769 A1 | 8/2017 | Niehaus et al. | |
| 2019/0099092 A1 | 4/2019 | Zhang et al. | |
| 2019/0099093 A1 | 4/2019 | Tudose et al. | |
| 2019/0099094 A1 | 4/2019 | Zhang et al. | |

FOREIGN PATENT DOCUMENTS

| | | |
|---|---|---|
| KR | 10-1094163 | 12/2011 |
| WO | WO2016/135731 | 9/2016 |
| WO | 2019067568 | 4/2019 |

OTHER PUBLICATIONS

Ogedegbe, G., et al. "Principles and techniques of blood pressure measurement," Cardiol Clin., Nov. 2010, vol. 28(4), 55 pp.
Azomaterials, Silicone Rubber, Aug. 23, 2016, AzoMaterials LtD https://web.archive.org/web/20160823110748/https://www.azom.com/properties.aspx?ArticleID=920 (Year: 2016).
U.S. Office Action dated Dec. 6, 2019, in U.S. Appl. No. 15/855,932.
U.S. Office Action dated Dec. 31, 2019, in U.S. Appl. No. 15/855,985.
U.S. Office Action dated Jan. 9, 2020, in U.S. Appl. No. 15/855,986.
U.S. Final Office Action dated Apr. 16, 2020, in U.S. Appl. No. 15/855,932.
U.S. Final Office Action dated May 6, 2020, in U.S. Appl. No. 15/855,985.
U.S. Final Office Action dated May 11, 2020, in U.S. Appl. No. 15/855,986.
U.S. Office Action dated Sep. 25, 2020, in U.S. Appl. No. 15/855,932.
U.S. Notice of Allowance dated Jan. 26, 2021, in U.S. Appl. No. 15/855,932.
U.S. Office Action dated Oct. 27, 2020, in U.S. Appl. No. 15/855,985.
U.S. Notice of Allowance dated Aug. 31, 2020, in U.S. Appl. No. 15/855,986.
Supplementary European Search Report for application No. PCT/US2018/052892, dated Sep. 2, 2021, 12 pages.

* cited by examiner

Section C-C

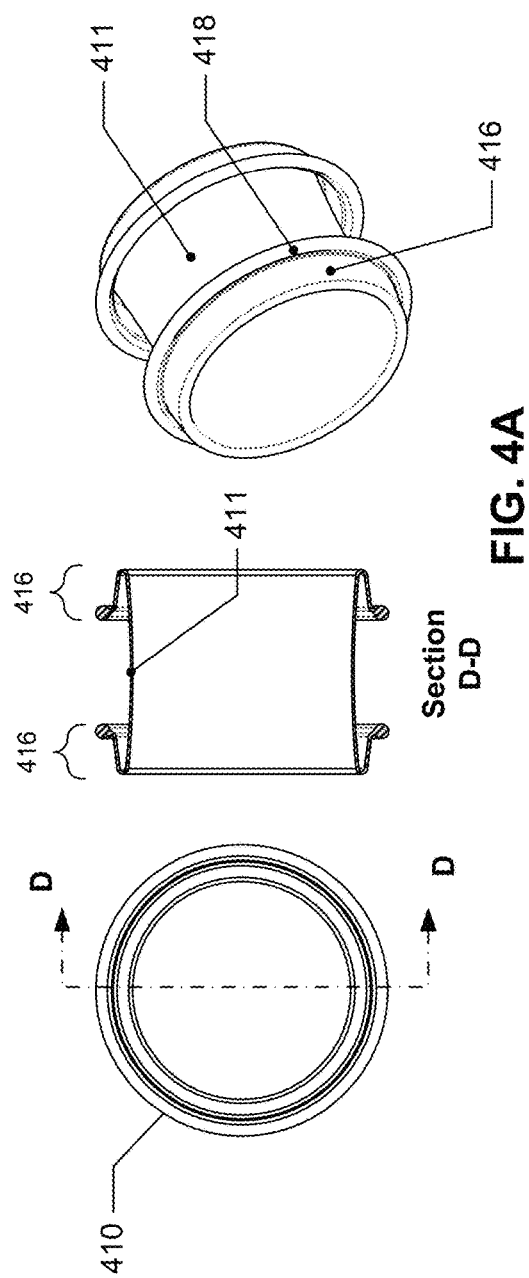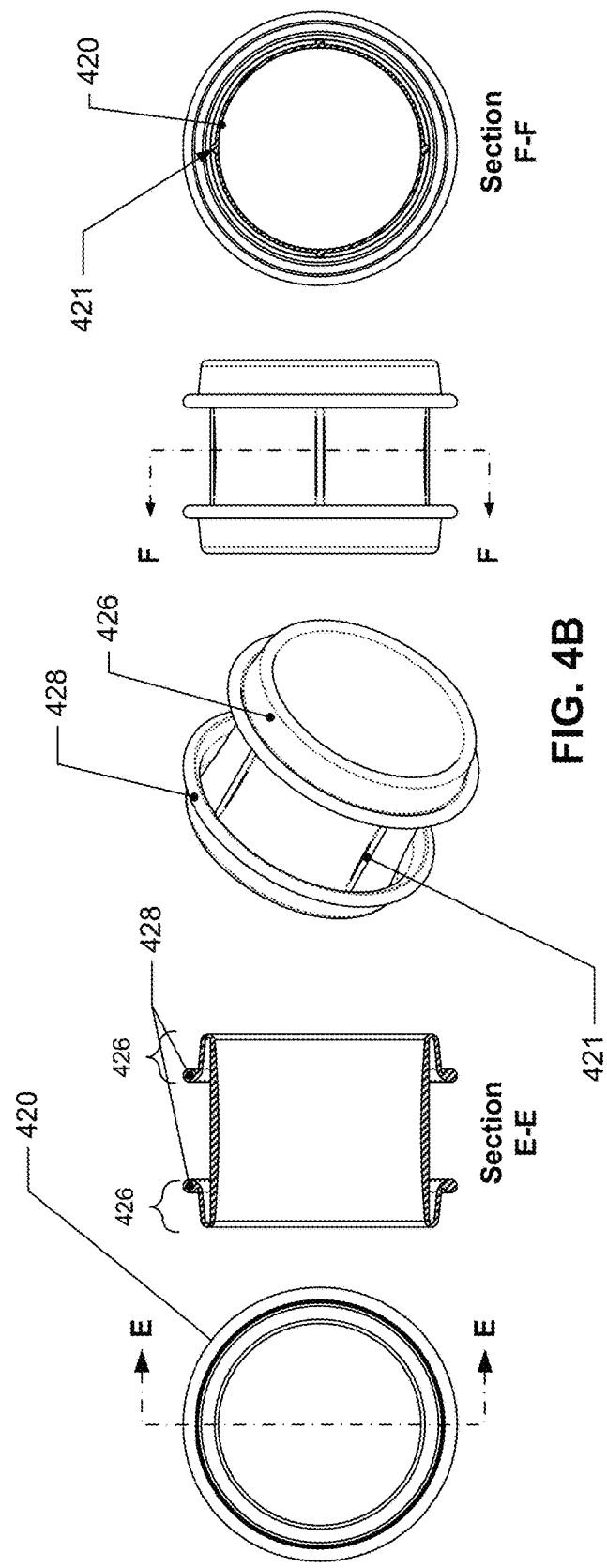
FIG. 4A
FIG. 4B

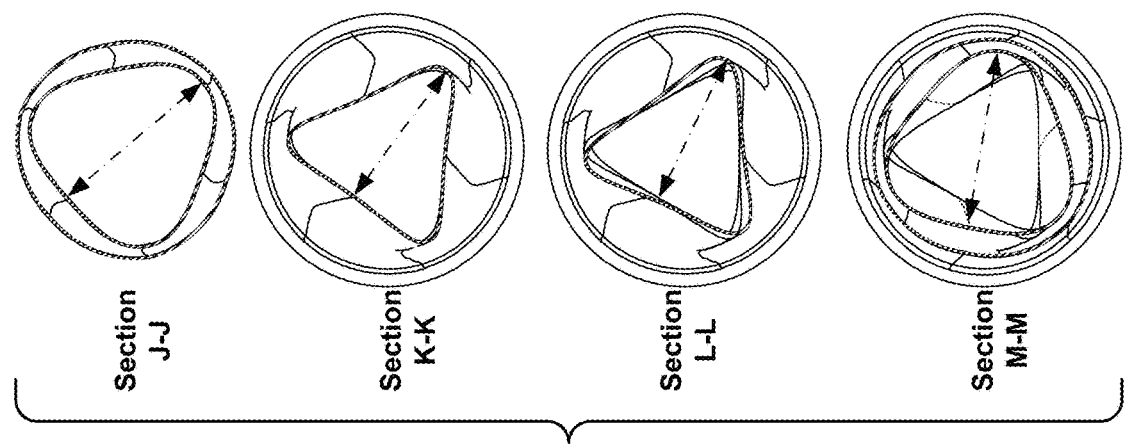
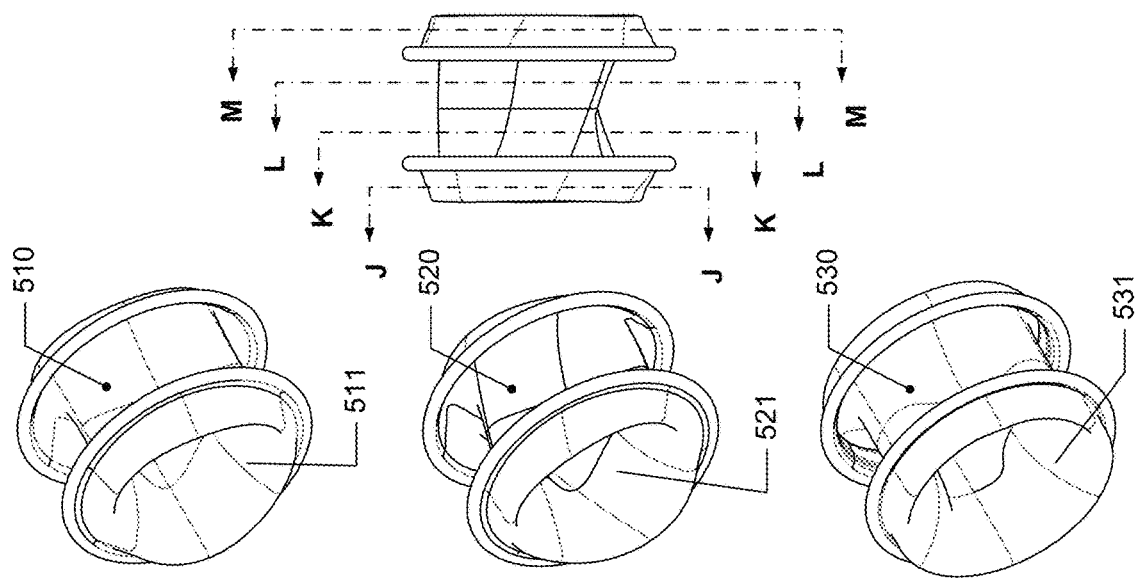
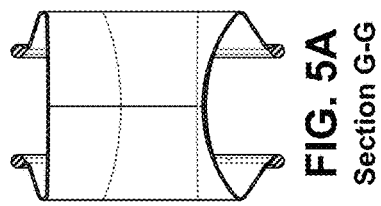
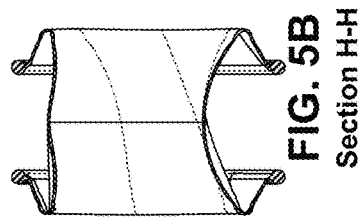
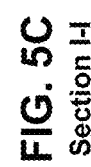
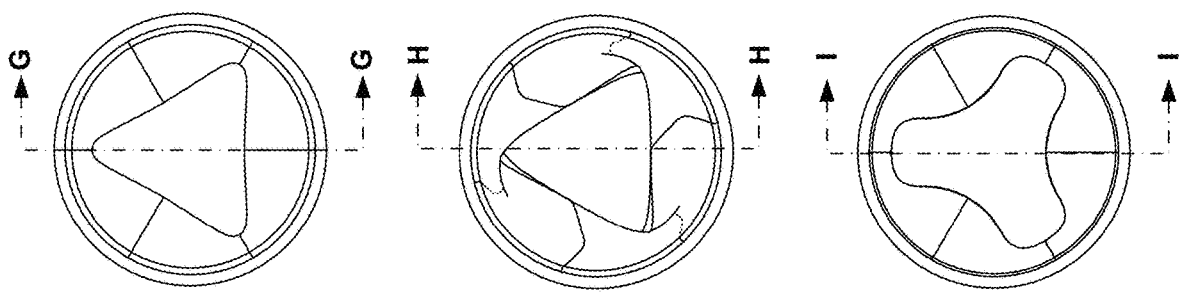

POSITION DETECTION OF BLOOD PRESSURE DEVICE

CROSS REFERENCE TO RELATED APPLICATIONS

This application is a continuation of and claims the benefit of priority under 35 U.S.C. § 120 to U.S. patent application Ser. No. 15/855,932, filed Dec. 27, 2017, titled "FINGER BLOOD PRESSURE CUFF," which, in turn, claims the benefit of priority under 35 U.S.C. § 119(e) to U.S. Provisional Patent Application No. 62/566,202, filed Sep. 29, 2017, and titled "FINGER BLOOD PRESSURE CUFF," each of which is hereby incorporated by reference herein in its entirety and for all purposes.

INTRODUCTION

Blood pressure is an important health indicator measured in both clinical and nonclinical settings. Many automated systems for measuring a user's blood pressure may use an oscillometric blood pressure measurement (OBPM) technique. Traditional OBPM systems inflate a bladder with air and squeeze an artery with a varying amount of pressure, and the OBPM systems "listen" for the strength of user's heart beat against that pressure. OBPM systems are widely used, primarily because they are easier to use than other alternative methods and do not require a trained operator as compared to the traditional auscultatory method.

The pressure signal captured by OBPM is affected by hydrostatic pressure, which is affected by cuff placement relative to the heart. Some existing OBPM systems require placement of the measuring device around the upper arm at the heart level to cause the hydrostatic pressure to be nearly equivalent to the hydrostatic pressure at the heart. Other existing OBPM systems can be placed around the wrist, but such OBPM systems may be more susceptible to variations in hydrostatic pressure, e.g., due to elevation differences between the heart and the measurement location.

Arm cuff OBPM systems tend to be large, cumbersome, and uncomfortable. Wrist-worn OBPM systems may be more portable but tend to be less reliable and less accurate than arm cuff OBPM systems.

SUMMARY

Details of one or more implementations of the subject matter described in this specification are set forth in the accompanying drawings and the description below. Other features, aspects, and advantages will become apparent from the description, the drawings, and the claims.

One aspect of the disclosure relates to a device for estimating a user's blood pressure. The device includes a housing having a hole sized to receive a human finger, a pump, an inflatable elastic bladder disposed about an inward-facing surface of the hole and defining, at least in part, a pressurizable volume in fluidic communication with the pump, and a pressure sensor in fluidic communication with the pressurizable volume and configured to produce pressure data indicative of a pressure within the pressurizable volume as a function of time. The pump is configured to pressurize the pressurizable volume and cause the inflatable elastic bladder to expand towards the center of the hole and contact a user's finger when the user's finger is positioned in the opening of the device and the pump is activated.

In some implementations, the device further includes a ring-shaped structure disposed within the hole and encircling the inflatable elastic bladder, the ring-shaped structure further defining, at least in part, the pressurizable volume. The ring-shaped structure may have a first end and a second end with a substantially cylindrical inner surface spanning between the first end and the second end, the inflatable elastic bladder including a first seal bead and a second seal bead with a membrane structurally interposed between the first seal bead and the second seal bead, the first seal bead being sealed against the first end of the ring-shaped structure and the second seal bead being sealed against the second end of the ring-shaped structure, the ring shaped structure including one or more ports that fluidically connect the pressurizable volume with the pump. The one or more ports may pass through the ring-shaped structure and may be configured to fluidically connect the pressurizable volume with an annular passage encircling the ring-shaped structure and in fluidic communication with the pump. In some implementations, the pressurizable volume has a continuous annular shape. In some implementations, the inflatable elastic bladder includes two or more lobes substantially symmetrically distributed about a center axis of the hole, each lobe including a middle portion bracketed between two end portions, the middle portion of each lobe extending closer to the center axis than the corresponding end portions of that lobe when the pressurizable volume is at zero gauge pressure. The device may further include a controller that is configured to control the pump to increase the pressure within the pressurizable volume from a first pressure to a second pressure, thereby causing the inflatable elastic bladder to expand towards the center axis, and to cause a notification to be provided indicating that the user should insert their finger into the hole responsive to an indication from the pressure sensor that the pressurizable volume is at the second pressure, that is configured to control the pump to further increase the pressure in the pressurizable volume beyond the second pressure, that is configured to monitor the pressure data from the pressure sensor to determine when the pressure within the pressurizable volume reaches a third pressure at which pulsatile variations in the pressure within the pressurizable volume are detectable in the pressure data, that is configured to control the pump to further increase the pressure in the pressurizable volume to a fourth pressure at which the pulsatile variations in the pressure within the pressurizable volume decrease to a first predetermined level, that is configured to determine systolic blood pressure data based on the fourth pressure, and that is configured to determine diastolic blood pressure data based on the third pressure. The inflatable elastic bladder may have a helical twist about the center axis of the hole. In some implementations, the inflatable elastic bladder is made of silicone or other elastomer having a Young's modulus selected from a group consisting of: between about 0.001 GPa to about 0.1 GPa and between about 0.003 GPa and about 0.05 GPa. In some implementations, the inflatable elastic bladder includes a membrane section that transitions to a bellows section at opposing ends, each bellows section extending back towards the other bellows section from where that bellows section transitioned to the membrane section, each bellows section terminating in a seal bead that encircles the membrane section. In some implementations, the housing includes a circumferential lip that extends around the hole, forms an aperture smaller than the hole when viewed along a center axis of the hole, and obscures a portion of the inflatable elastic bladder from view when viewed along the center axis with the device oriented such that the inflatable elastic bladder is behind the circumferential lip.

Another aspect of the disclosure relates to a device for estimating a user's blood pressure. The device includes an inflatable bladder defining, at least in part, a pressurizable volume, a pump in fluidic communication with the inflatable bladder and configured to pressurize the pressurizable volume and cause the inflatable bladder to inflate and contact a user's appendage when the pump is activated, and a pressure sensor in fluidic communication with the inflatable bladder and configured to produce pressure data indicative of pressure within the pressurizable volume as a function of time. An inflation rate of the pump is controllable by controlling at least one of a duty cycle, a voltage, or a drive frequency.

In some implementations, the inflatable bladder is an inflatable elastic bladder disposed about an inward-facing surface of a hole in the device, where the pump is configured to pressurize the pressurizable volume when a user's finger is positioned in the hole of the device. In some implementations, the inflation rate of the pump is controlled to be between about 1 mmHg per second and about 10 mmHg per second. In some implementations, the device further includes a controller coupled with the pump, where the controller is configured to control a duty cycle of the pump. The controller may be configured to increase the duty cycle of the pump from a first duty cycle to a second duty cycle at a first selected rate. The first duty cycle may be less than 100% duty cycle and the second duty cycle may be 100% duty cycle, the first selected rate being between about 0.1% and about 20% increase in duty cycle per second. The controller may be configured to increase the duty cycle of the pump from the second duty cycle to a third duty cycle at a second selected rate. In some implementations, the controller is configured to dynamically change the duty cycle of the pump based at least in part on the pressure data of the pressurizable volume. In some implementations, the device further includes a controller coupled to the pump, where the controller is configured to control a peak-to-peak voltage ($V_{pp}$) of the pump. The controller may be configured to increase the peak-to-peak voltage of the pump from a first peak-to-peak voltage to a second peak-to-peak voltage at a selected rate. In some implementations, a drive frequency of the pump is equal to or greater than about 23 kHz.

Another aspect of the disclosure relates to a method of controlling an inflation rate of an inflatable bladder. The method includes causing the inflatable bladder to inflate using a pump and contact a user's appendage, and increasing a duty cycle of the pump from a first duty cycle to a second duty cycle at a first selected rate.

In some implementations, the first duty cycle is less than 100% duty cycle and the second duty cycle is 100% duty cycle, the first selected rate being between about 0.1% and about 20% increase in duty cycle per second. In some implementations, the method further includes obtaining pressure data indicative of a pressure within a pressurizable volume of the inflatable bladder as a function of time, and increasing the duty cycle of the pump from the second duty cycle to a third duty cycle at a second selected rate, where increasing the duty cycle from the second duty cycle to the third duty cycle occurs when the pressure within the pressurizable volume reaches a threshold pressure. In some implementations, the method further includes obtaining pressure data indicative of pressure within a pressurizable volume of the inflatable bladder as a function of time, and dynamically changing the duty cycle of the pump based at least in part on the pressure data of the pressurizable volume.

Another aspect of the disclosure relates to a device for estimating a user's blood pressure. The device includes an inflatable bladder defining, at least in part, a pressurizable volume, a pump in fluidic communication with the inflatable bladder and configured to pressurize the pressurizable volume and cause the inflatable bladder to inflate and contact a user's appendage when the pump is activated, a pressure sensor in fluidic communication with the inflatable bladder and configured to produce pressure data indicative of pressure within the pressurizable volume as a function of time, where the pressure data includes oscillometric data in a first pressure profile and pulse information in a second pressure profile, and a controller coupled to the pump. The controller is configured to cause the pump to pressurize the pressurizable volume to a first pressure greater than a maximum amplitude pressure of the oscillometric data in the first pressure profile.

In some implementations, the inflatable bladder is an inflatable elastic bladder disposed about an inward-facing surface of a hole in the device, wherein the pump is configured to pressurize the pressurizable volume when a user's finger is positioned in the hole of the device. In some implementations, the first pressure profile is indicative of the pressure within the pressurizable volume up to the first pressure as a function of time, and the second pressure profile is indicative of the pressure within the pressurizable volume as a function of time after reaching the first pressure. In some implementations, the controller is further configured to cause the pump to deflate the inflatable bladder so that a pressure within the pressurizable volume reaches a target pressure less than the first pressure after reaching the first pressure. The controller may be configured to cause the pump to inflate the inflatable bladder so that a pressure within the pressurizable volume reaches a second pressure in the second pressure profile from the target pressure, where the second pressure is based at least in part on information from the oscillometric data in the first pressure profile. In some implementations, the controller may be configured to maintain the pressurizable volume at the second pressure for a duration sufficient to produce the pulse information in the second pressure profile. The duration for maintaining the pressurizable volume at the second pressure may be between about 1 second and about 15 seconds. In some implementations, the controller is further configured to maintain the pressurizable volume at the target pressure for a duration sufficient to obtain the pulse information in the second pressure profile, wherein the target pressure is based at least in part on information from the oscillometric data in the first pressure profile. In some implementations, the controller is further configured to analyze the pulse information in the second pressure profile to determine one or more of pulse wave analysis (PWA) features, arterial compliance, respiration, and atrial fibrillation.

Another aspect of the disclosure relates to a method of estimating a user's blood pressure. The method includes causing inflation of an inflatable bladder using a pump to contact a user's appendage, obtaining pressure data indicative of pressure within a pressurizable volume of the inflatable bladder as a function of time, where the pressure data includes oscillometric data in a first pressure profile, sustaining inflation of the inflatable bladder so that a pressure in the pressurizable volume reaches a first pressure greater than a maximum amplitude pressure of the oscillometric data in the first pressure profile, and causing deflation of the inflatable bladder so that the pressure in the pressurizable volume reaches a target pressure from the first pressure. The target pressure is based at least in part on information from the oscillometric data in the first pressure profile.

In some implementations, the method further includes maintaining the pressurizable volume at the target pressure for a duration between about 1 second and about 15 seconds. The pressure data may further include pulse information in a second pressure profile, where the pulse information is obtained when the pressurizable volume is maintained at the target pressure.

Another aspect of the disclosure relates to a method of estimating a user's blood pressure. The method includes causing inflation of an inflatable bladder using a pump to contact a user's appendage, obtaining pressure data indicative of pressure within a pressurizable volume of the inflatable bladder as a function of time, where the pressure data includes oscillometric data in a first pressure profile, sustaining inflation of the inflatable bladder so that a pressure in the pressurizable volume reaches a first pressure greater than a maximum amplitude pressure of the oscillometric data in the first pressure profile, causing deflation of the inflatable bladder from the first pressure, and causing inflation of the inflatable bladder so that the pressure of the pressurizable volume reaches a second pressure. The second pressure is based at least in part on information from the oscillometric data in the first pressure profile.

In some implementations, the method further includes maintaining the pressurizable volume at the second pressure for a duration between about 1 second and about 15 seconds. The pressure data may further include pulse information in a second pressure profile, where the pulse information is obtained when the pressurizable volume is maintained at the second pressure.

Another aspect of the disclosure relates to a device for estimating a user's blood pressure. The device includes an inflatable bladder defining, at least in part, a pressurizable volume, a pump in fluidic communication with the inflatable bladder and configured to pressurize the pressurizable volume and cause the inflatable bladder to inflate and contact a user's appendage when the pump is activated, a pressure sensor in fluidic communication with the inflatable bladder and configured to produce pressure data indicative of pressure within the pressurizable volume as a function of time, and one or more accelerometers. The one or more accelerometers are configured to determine relative positioning of the device with respect to a user's heart.

In some implementations, the inflatable bladder is an inflatable elastic bladder disposed about an inward-facing surface of a hole in the device, wherein the pump is configured to pressurize the pressurizable volume when a user's finger is positioned in the hole of the device. In some implementations, the one or more accelerometers are further configured to determine whether the device is in motion or stationary. The device may further include a controller configured to initiate inflation of the inflatable bladder using the pump when the one or more accelerometers determine that the device is positioned within a threshold elevation with respect to the user's heart and is stationary for a threshold duration. The controller may be further configured to turn off the device or enter a power-saving mode when the one or more accelerometers determine that the device is not positioned within the threshold elevation with respect to the user's heart and is stationary for a sufficient duration. In some implementations, the one or more accelerometers are configured to determine relative positioning of the device with respect to a user's heart by measuring an inclination about an axis that is orthogonal or substantially orthogonal to a vertical axis, the inclination including a roll angle and a pitch angle, wherein each of the roll angle and the pitch angle is between about 0 degrees and about 30 degrees when the device is determined to be at approximately the same elevation as the user's heart. In some implementations, the device further includes one or more auscultation sensors configured to acoustically determine a location of the user's heart. In some implementations, the device further includes one or more optical sensors for determining that the user's finger is positioned within a hole of the device, where the inflatable bladder is disposed about an inward-facing surface of the hole of the device. In some implementations, the device further includes one or more feedback devices configured to communicate to a user a positioning of the device relative to the user's heart, wherein the one or more feedback devices include at least one of a speaker for audio feedback, a light-emitting diode (LED) for optical feedback, a display for visual feedback, and a motor for haptic feedback.

Another aspect of the disclosure relates to a device for estimating a user's blood pressure. The device includes an inflatable bladder defining, at least in part, a pressurizable volume, a pump in fluidic communication with the inflatable bladder and configured to pressurize the pressurizable volume and cause the inflatable bladder to inflate and contact a user's appendage when the pump is activated, a pressure sensor in fluidic communication with the inflatable bladder and configured to produce pressure data indicative of pressure within the pressurizable volume as a function of time, and one or more proximity sensors. The one or more proximity sensors are configured to determine that the device is positioned proximate to a user's heart.

In some implementations, the inflatable bladder is an inflatable elastic bladder disposed about an inward-facing surface of a hole in the device, wherein the pump is configured to pressurize the pressurizable volume when a user's finger is positioned in the hole of the device. In some implementations, the one or more proximity sensors include one or both of an auscultation sensor and a microphone configured to acoustically determine proximity of the user's heart. In some implementations, the device further includes one or more accelerometers configured to determine whether the device is in motion or stationary. The device may further include a controller configured to initiate inflation of the inflatable bladder using the pump when the one or more proximity sensors determine that the device is positioned proximate to the user's heart and the one or more accelerometers determine that the device is stationary for a threshold duration.

These are other implementations are described in further detail with reference to the Figures and the detailed description below.

BRIEF DESCRIPTION OF THE DRAWINGS

FIG. 4A shows an example inflatable elastic bladder according to some implementations; front, side section, and isometric views, from left to right, are depicted.

FIG. 4B shows an example inflatable elastic bladder according to some other implementations; front, side section, isometric, side, and front section views, from left to right, are depicted.

FIG. 5A shows an example inflatable elastic bladder with three inflatable lobes according to some implementations; front, side section, and isometric views, from left to right, are depicted.

FIG. 5B shows an example inflatable elastic bladder with three inflatable twisted lobes according to some implementations; front, side section, isometric, and side views, from left to right, are depicted, as well as multiple front section views along the right side of the Figure.

FIG. 5C shows an example inflatable elastic bladder with pre-inflated lobes according to some implementations; front, side section, and isometric views, from left to right, are depicted.

DETAILED DESCRIPTION

In contrast to traditional blood pressure cuffs placed around a user's arm or a user's wrist, the present disclosure relates to a blood pressure cuff placed around a user's finger. A finger blood pressure cuff may offer advantages over traditional wrist or arm blood pressure cuffs because it may be less bulky, easier to use, more portable, more compact, less obtrusive, and more comfortable to the user. However, measuring blood pressure at a user's finger is typically not regarded as accurate and reliable because of its further distance from the user's heart as compared with upper arm and wrist-located measurements. As used herein, a finger blood pressure cuff refers to any system, device, or apparatus that wraps around a user's finger and is configured to estimate a blood pressure of the user.

In an embodiment, a finger blood pressure cuff may include a rigid ring-shaped structure and an inflatable elastic bladder configured to inflate inwards towards a center of the ring-shaped structure and contact a user's finger that has been inserted through the ring-shaped structure. The elastic bladder may be inflated to pressurize it and squeeze the user's finger and temporarily occlude blood flow in the user's finger. Some examples of the finger blood pressure cuff may include one or more sensors for detecting that the user's finger is proximate to the user's chest. The finger blood pressure cuff may, during use, generate pressure data corresponding to an applied pressure on the user's finger; such data may then be analyzed, either by the finger blood pressure cuff or another device that receives data from the cuff, in order to obtain measurements of blood pressure and other cardiovascular data, e.g., heart rate.

Example Structure of the Finger Blood Pressure Cuff

Figure 1:
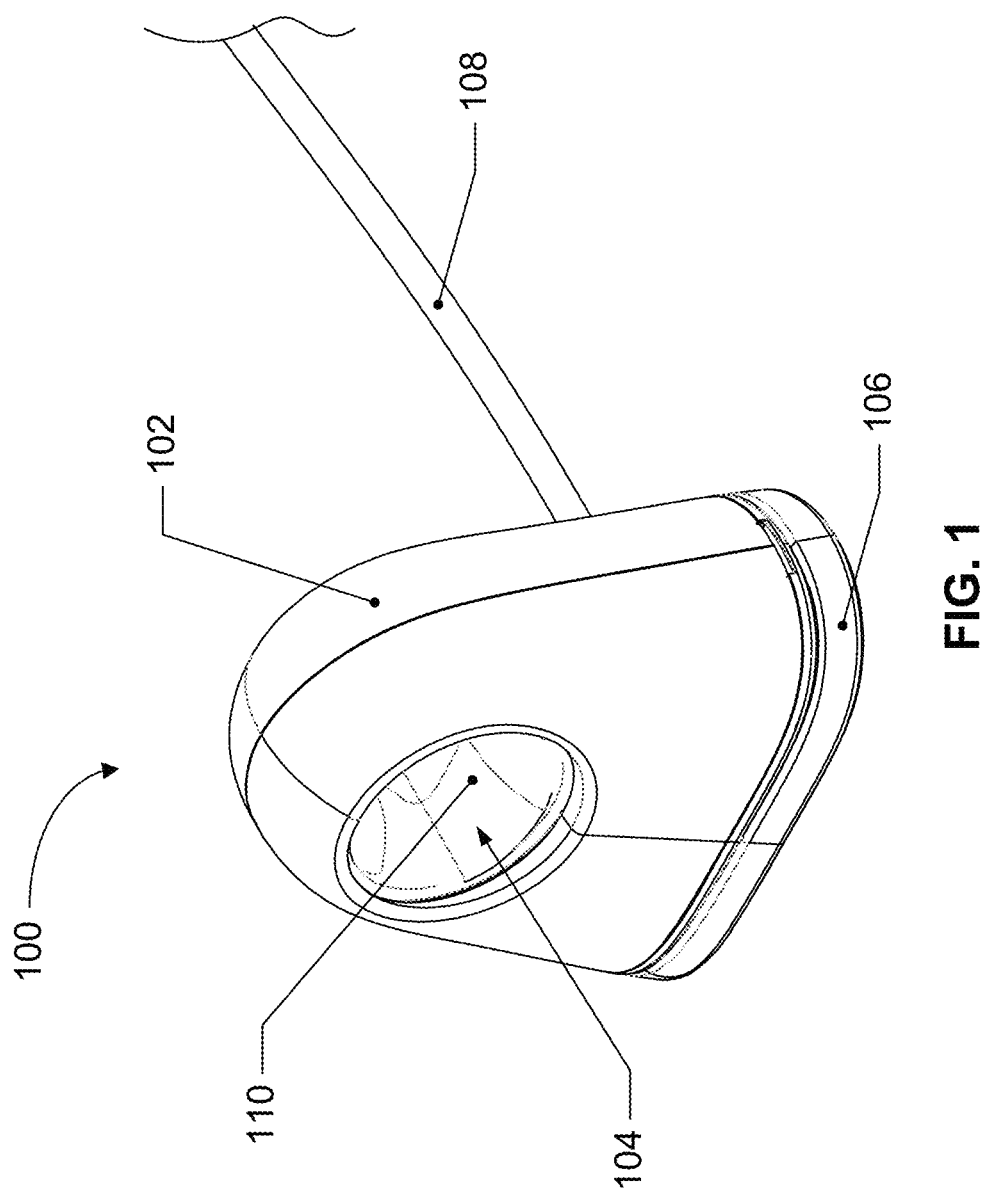
FIG. 1 shows a perspective view of an example finger blood pressure cuff according to some implementations.

FIG. 1 shows a perspective view of an example finger blood pressure cuff 100 according to some implementations. The finger blood pressure cuff 100 may include a housing 102 with an opening or hole 104 through which a user's finger can be inserted. A generally rigid ring-shaped structure and an inflatable elastic bladder 110 may be disposed within the opening 104 of the housing 102. The housing 102 may enclose one or more components associated with performing the operations of the finger blood pressure cuff 100, such as one or more of a controller or control unit, a pressure sensor, one or more inertial measurement units (e.g., multi-axis accelerometers, gyroscopes, etc.), a piezoelectric pump (or a different kind of pump), a battery or other power source, and other circuitry. The housing 102 may be supported on a base 106, where the base 106 is connected to a power cable 108. Alternatively, the housing 102 may simply have a connector port for connecting to a power cable directly.

Figure 2:
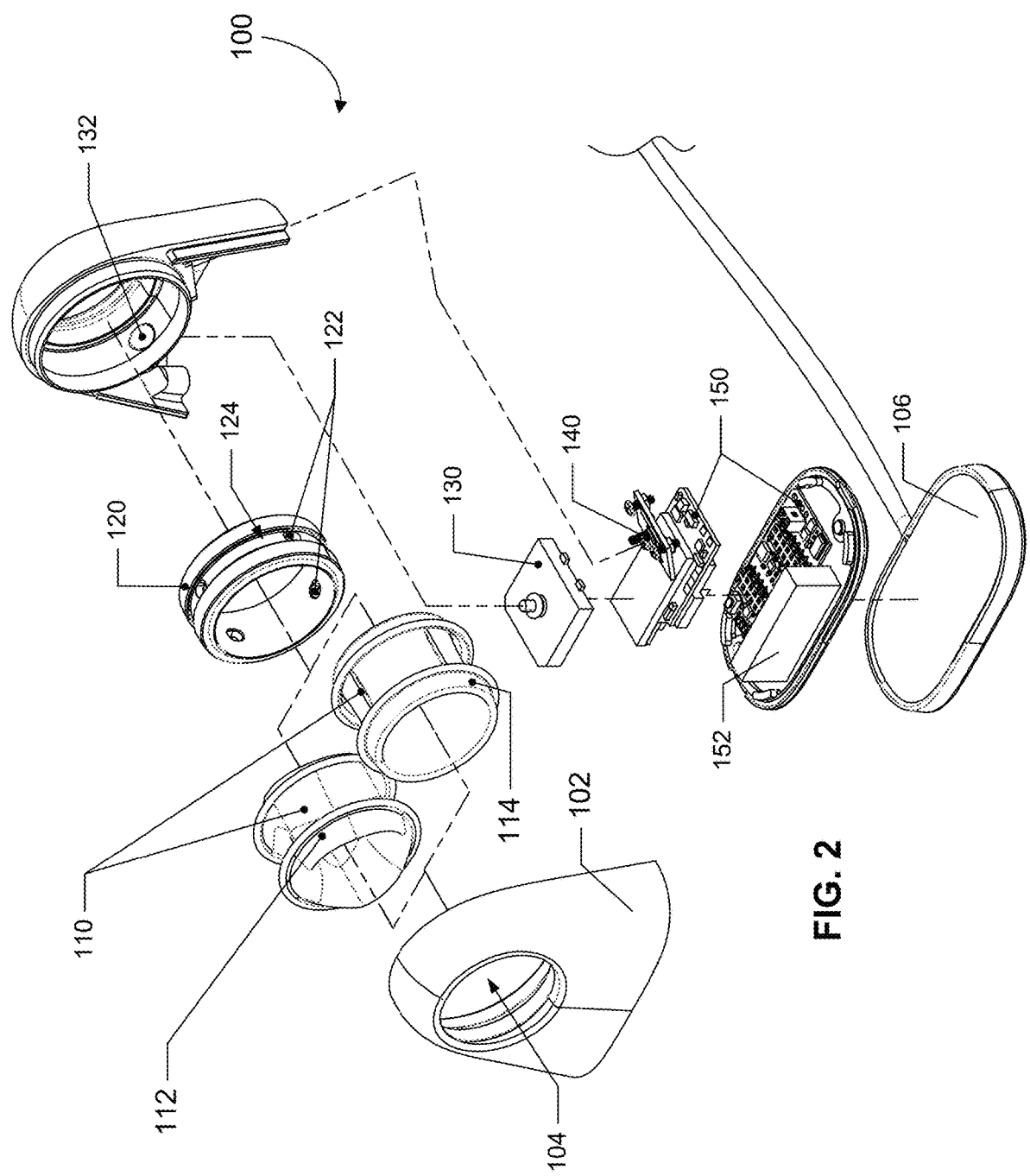
FIG. 2 shows a perspective view of various components of an example finger blood pressure cuff according to some implementations.

FIG. 2 shows a perspective view of various components of an example finger blood pressure cuff 100 according to some implementations. The finger blood pressure cuff 100 includes a housing 102 with an opening 104 for accommodating a ring-shaped structure 112 and an inflatable elastic bladder 110 within the opening 104 so that the inflatable elastic bladder 110 is disposed about an inward-facing surface of the hole or opening 104 (thus, the inflatable elastic bladder 110 appears to provide the interior surface of the hole or opening 104 when viewed by a user). The ring-shaped structure 112 may include a hard, rigid, or semi-rigid outer ring circumferentially disposed around the inflatable elastic bladder 110. The ring-shaped structure 112 may have a size based on a user's finger size. The inflatable elastic bladder 110 may, in certain implementations, include a continuous, inflatable, generally annular volume 114. Or, the inflatable elastic bladder may, in certain implementations, include two or more inflatable volumes 112 about a center of the opening 104 (which may be compartmentalized or may alternatively, as in the depicted example, define a contiguous interior bladder volume). The two or more inflatable volumes 112 may be two or more inflatable lobes symmetrically distributed about the center of the opening. However, it will be understood that in some implementations, the two or more inflatable lobes may be non-symmetrically distributed about the center of the opening. In some implementations, the inflatable elastic bladder 110 may comprise three inflatable lobes. Upon inflation, e.g., when the pump is used to pressurize the pressurizable volume, the inflatable elastic bladder 110 may expand inwards towards the center of the hole or opening 104 and press against a user's finger that is inserted in the opening 104 and provide sufficient arterial clamping to at least temporarily occlude blood flow in the user's finger.

As noted above, the ring-shaped structure 120 and the inflatable elastic bladder 110 may, in combination, define a pressurizable volume that may be pressurized in order to cause the inflatable elastic bladder 110 to expand in towards the center of the ring-shaped structure 120. In many implementations, the ring-shaped structure 120 and the inflatable elastic bladder 110 may be generally radially or axially symmetric (with respect to the ring-shaped structure 120, it is to be understood that such general radial or axial symmetry may apply to the "interior-facing" surfaces, e.g., those surfaces that face towards the interior of the ring shape, and that the remainder of the ring-shaped structure may exhibit a lack of symmetry and be other than ring-shaped), with the center axes of both components generally aligned and with the ring-shaped structure 120 encircling the inflatable elastic bladder 110. Put another way, the ring-shaped structure 120 may provide a rigid framework that supports or helps support the inflatable elastic bladder 110 and may also provide a ring-shaped, rigid surface that defines part of the pressurizable volume of the bladder 110, with the majority of the remainder of the pressurizable volume of the bladder 110 being provided by the inflatable elastic bladder 110.

Several components may be enclosed within the housing 102 of the finger blood pressure cuff 100. As shown in FIG. 2, the finger blood pressure cuff 100 may include a pump 130 such as a piezoelectric pump that is fluidically connected with the pressurizable volume (which may also be referred to as a "bladder volume" or the like) of the inflatable elastic bladder 110 so that the pump 130 can pressurize the pressurizable volume and inflate the inflatable elastic bladder 110. The pump 130 may be fluidically connected with the inflatable elastic bladder 110 via a pump inlet/outlet 132 in the housing 102 and via one or more ports 122 in the ring-shaped structure 120. The ports 122 may be holes or openings in the ring-shaped structure 120, where the holes or openings may be positioned in an annular passage 124 of the ring-shaped structure 120. While two alternative inflatable elastic bladders 110 are shown in FIG. 2—only one would be used in a particular finger blood pressure cuff 100, though both are shown in this example figure. The various inflatable elastic bladders 110 may be interchangeable and thereby capable of being installed in, and removed from, the housing 102. The finger blood pressure cuff 100 may further include a pressure sensor 140 that is also fluidically connected with the pressurizable volume of the inflatable elastic bladder 110 to allow measurement of the pressure within the pressurizable volume over time. The finger blood pressure cuff 100 may further include a controller or control unit that is configured to control the pump 130 and to receive and process data from the pressure sensor 140, where the controller or control unit along with other circuitry may be mounted on one or more printed circuit boards (PCBs) 150. The finger blood pressure cuff 100 may further include a battery 152 for powering the finger blood pressure cuff 100. As shown in FIG. 2, a charger may be configured to recharge the battery 152, e.g., via inductive charging or other charging technique, and may be incorporated into a base 106 on which the blood pressure cuff 100 may be placed. The blood pressure cuff 100 may also include one or more communication interfaces, e.g., USB, Bluetooth, etc., that may be used to send data, either directly or by way of one or more intermediary devices, from the device to another device, e.g., a smartphone, computer, or remote server. The data may be processed using the processor or processors within the housing 102, processors or a processor in another device, e.g., a server or smartphone, or a combination of such options.

Figure 3A:
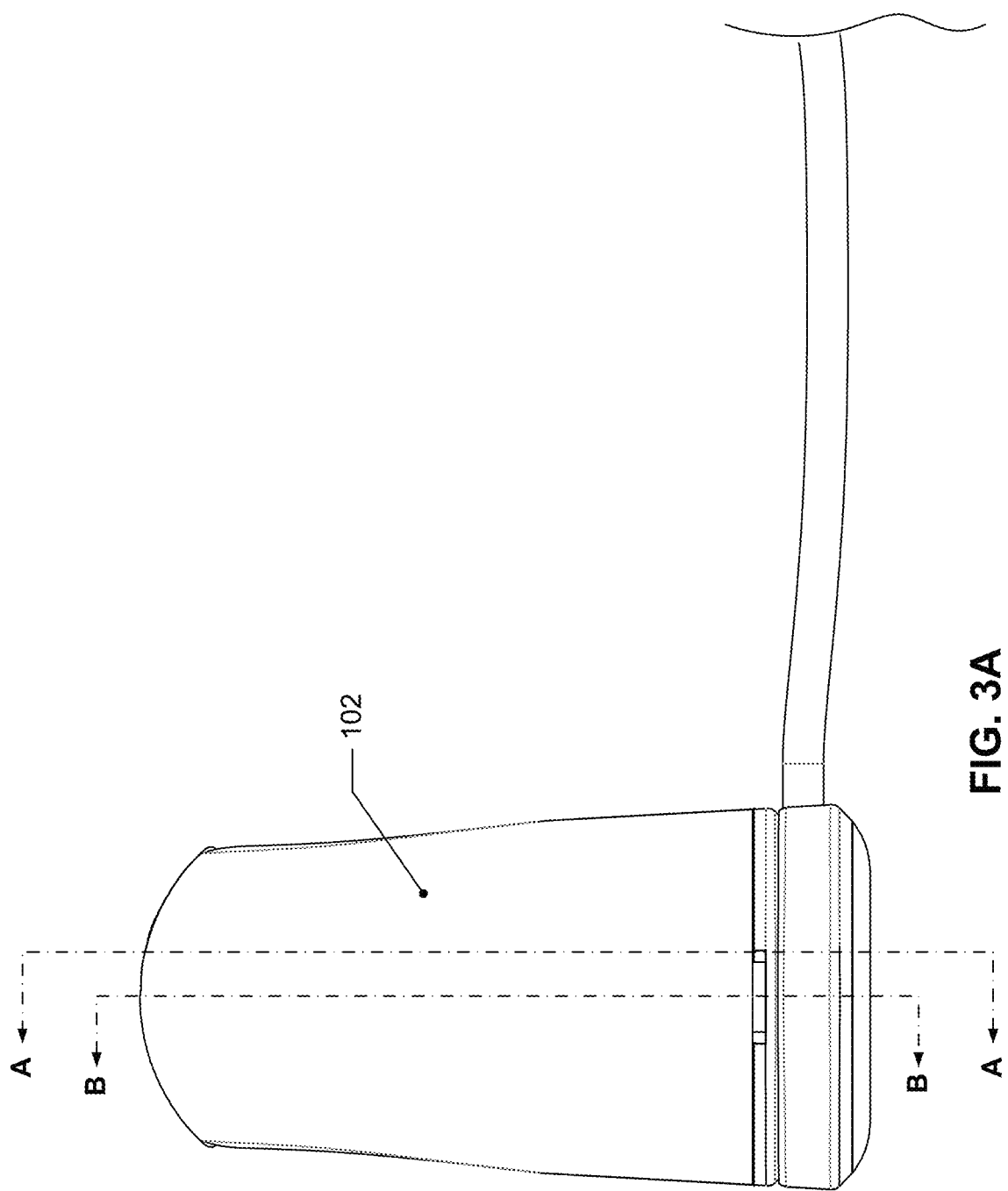
FIG. 3A shows a side view of an example finger blood pressure cuff according to some implementations.
Figure 3B:
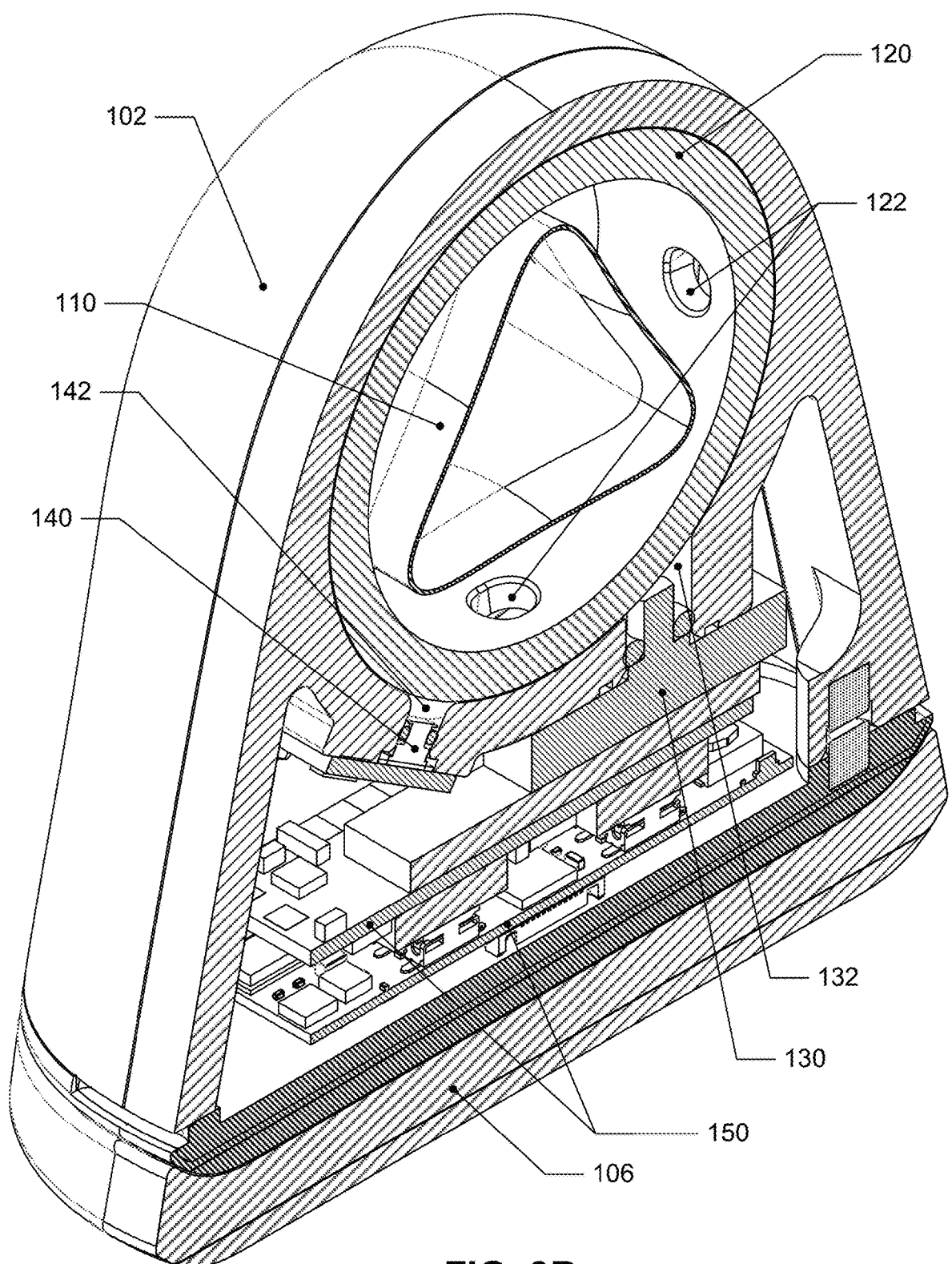
FIG. 3B shows a cross-sectional perspective view of the finger blood pressure cuff of FIG. 3A cut along lines A-A.
Figure 3C:
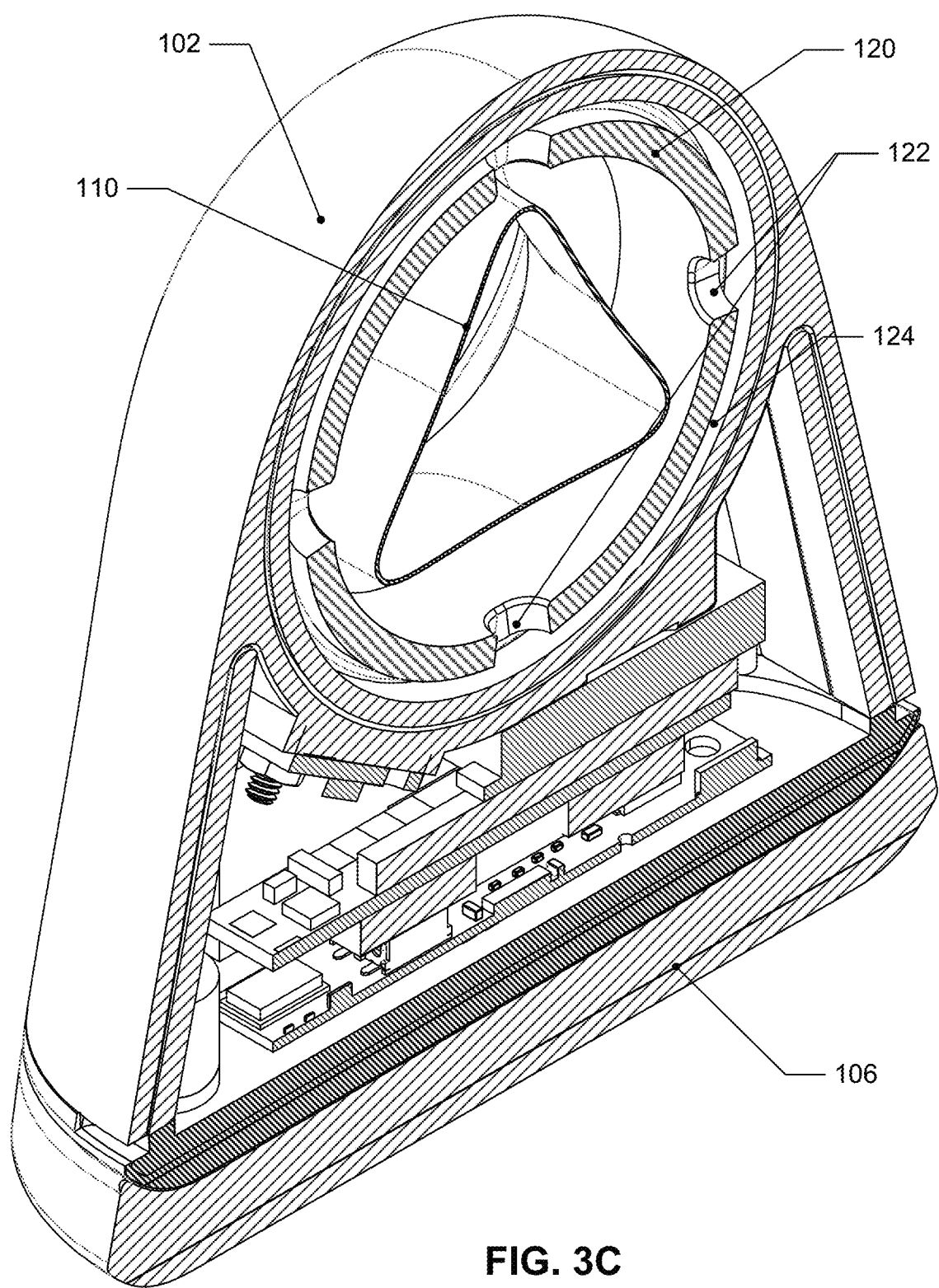
FIG. 3C shows a cross-sectional perspective view of the finger blood pressure cuff of FIG. 3A cut along lines B-B.
Figure 3E:
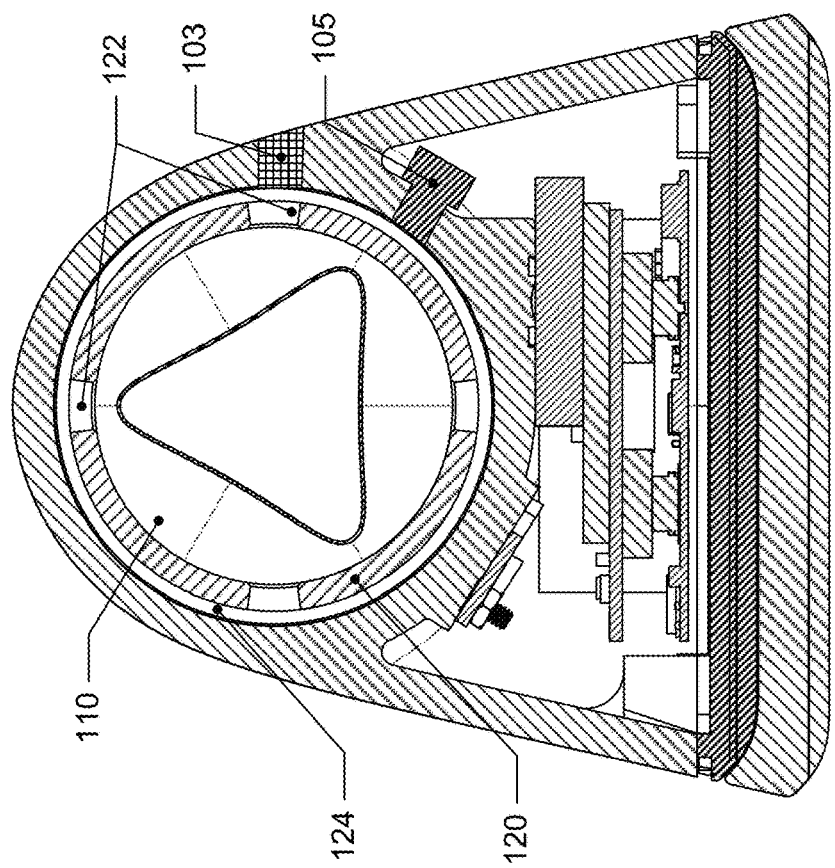
FIG. 3E shows a cross-sectional side view of the finger blood pressure cuff of FIG. 3A cut along lines B-B.
Figure 3D:
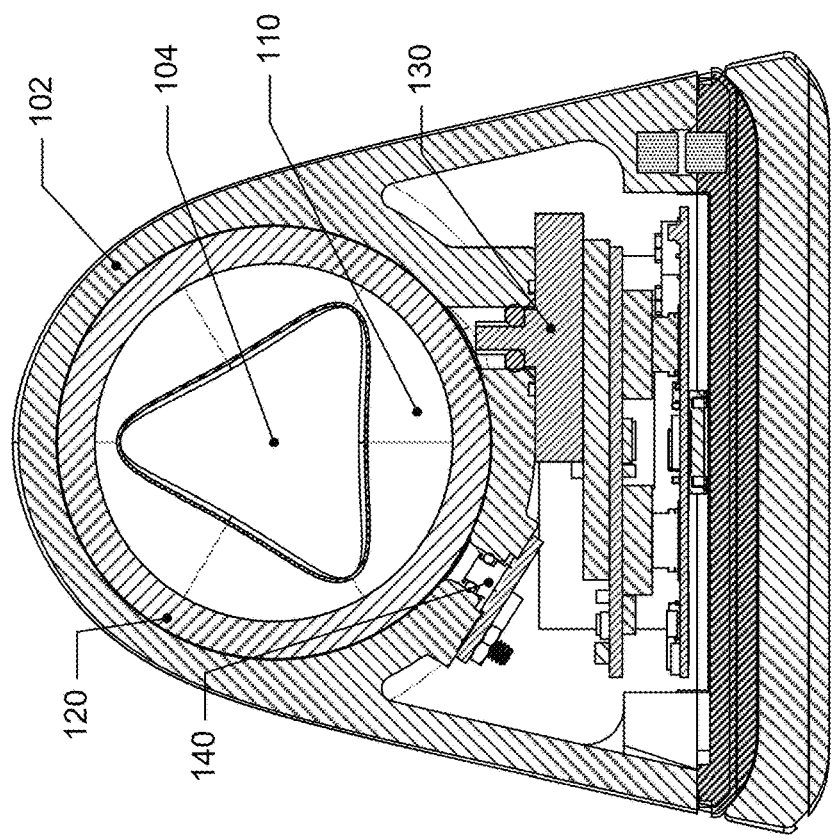
FIG. 3D shows a cross-sectional side view of the finger blood pressure cuff of FIG. 3A cut along lines A-A.

FIG. 3A shows a side view of an example finger blood pressure cuff. FIG. 3B shows a cross-sectional perspective view of the finger blood pressure cuff of FIG. 3A cut along lines A-A. FIG. 3C shows a cross-sectional perspective view of the finger blood pressure cuff of FIG. 3A cut along lines B-B. FIG. 3D shows a cross-sectional side view of the finger blood pressure cuff of FIG. 3A cut along lines A-A. FIG. 3E shows a cross-sectional side view of the finger blood pressure cuff of FIG. 3A cut along lines B-B.

In FIGS. 3B-3E, an opening 104 of a housing 102 of the finger blood pressure cuff 100 accommodates an inflatable elastic bladder 110. The inflatable elastic bladder 110 occupies a volume within the opening 104. In some implementations, the inflatable elastic bladder 110 may have a generally triangular shape along a portion of its length to provide a three-lobed design. As shown in FIGS. 3B-3E, the inflatable elastic bladder 110 includes three lobes that are each configured to expand towards a center of the opening 104 upon inflation. The use of two or more lobes provides a centering effect on the finger and encourages the finger to move towards the center of the opening 104, thereby promoting even inflation of the lobes, and more radially uniform application of pressure on the finger by the bladder 110. Moreover, the use of two or more lobes reduces inaccuracies that may result from a user's finger being small relative to the inflatable elastic bladder 110. Without multiple lobes, a bladder will stretch and a tensile strength of the bladder 110 supports some of the internal pressure, thereby reducing pressure on the finger. This effect is more significant with smaller fingers and is minimized with the application of multiple lobes.

Inflation air may be provided from a pump 130 (e.g., piezoelectric pump) through a plurality of holes or ports 122 in the ring-shaped structure 120 to inflate the inflatable lobes of the elastic bladder 110. It should be understood that alternative designs may utilize a liquid, e.g., water or oil, instead of air (or may use a gas other than air, if desired) and may utilize pumps that may be designed for use with liquids instead of gases—in such cases, a reservoir, e.g., another expandable bladder, may be used to store the working liquid that is not within the inflatable bladder mechanism. One or more pressure sensors 140 in the finger blood pressure cuff 100 may be configured to measure the pressure within the pressurizable volume of the inflatable elastic bladder 110, which is generally proportionate to the pressure actually applied by the bladder 110 on a user's finger positioned in the opening 104. Accordingly, the pressure sensor 140 may be used to produce pressure data indicative of the pressure within the pressurizable volume of the inflatable elastic bladder 110. The sensed pressure within the pressurizable volume is generally proportionate to the actually applied pressure on the user's finger positioned in the opening 104. Such pressure data may be used to provide a "pressure profile" that visually represents the pressure measured within the pressurizable volume of the inflatable elastic bladder 110 over time. As shown in FIGS. 3B and 3D, a pressure sensor 140 may be contained within the housing 102 and adjacent to the ring-shaped structure 120 and the inflatable elastic bladder 110. Each of the pressure sensor(s) 140 and the pressurizing pump(s) 130 may be electrically coupled with a controller. The controller may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. In some implementations, the controller includes a processor, where the processor may be controlled by computer-executable instructions stored in memory so as to provide functionality described herein. The processor and other circuitry may be provided on one or more PCBs 150 enclosed in the housing 102.

In some implementations, the inflatable elastic bladder 110 may be sealed or attached to the ring-shaped structure 120, where the seal or attachment may form a relatively airtight volume. While the inflatable elastic bladder 110 and ring-shaped structure 120 may form an airtight volume, it is understood that in some implementations the inflatable elastic bladder 110 and ring-shaped structure 120 may include a leakage point (e.g., designed-in leak) to reduce inflation speed and/or provide a controlled or "automatic" mode of deflation. In some implementations, the inflatable elastic bladder 110 may be welded or joined to the ring-shaped structure 120 via a thermoplastic material or thermoplastic coating on the inflatable elastic bladder 110. In some implementations, the inflatable elastic bladder 110 may be attached to the ring-shaped structure 120 by an adhesive or using a suitable chemical bonding technique.

Typical OBPM systems use inflatable bladders made of flexible, but generally inelastic, materials such as vinyl. However, the finger blood pressure cuff 100 of the present disclosure uses an inflatable bladder 110 made of an elastic material. In some implementations, the elastic material includes silicone or other elastomer having a Young's modulus between about 0.001 GPa and about 0.1 GPa or between about 0.003 GPa and about 0.05 GPa, which are orders of magnitude lower than that of materials like vinyl which are presently used in typical blood pressure cuffs. For example, the elastomer can have a Young's modulus of about 0.005 GPa. In the context of a finger cuff apparatus, pressure loss using an elastic material is smaller compared to using an inelastic material. Without being limited by any theory, the elastic material may provide flexibility to ensure that the pressure inside of the inflatable bladder 110 is optimally transferred to the user's finger to minimize pressure loss. Moreover, an inelastic material may have more folds and creases that allow the bladder material to fold over and press against itself, introducing additional sources of pressure loss from the material itself. As used herein, pressure loss refers to the difference between the internal pressure of the inflatable bladder (i.e., pressure used to inflate and stretch the bladder 110) and the externally applied pressure to the blood vessel of the user's finger. A reduced pressure loss using an elastic material may allow the finger blood pressure cuff 100 to be used on a wide range of fingers of different sizes with a negligible difference in signal output.

In some implementations, the inflatable elastic bladder 110 may be relatively thin, such as between about 0.1 mm and about 0.75 mm thick or between about 0.25 mm and about 0.5 mm thick. Thin inflatable elastic bladders 110 may reduce pressure loss while permitting expansion of the inflatable elastic bladder 110.

In some implementations, the elastic material may be treated or coated to reduce a tackiness of the elastic bladder. For example, the elastic material may be treated by ultraviolet (UV) oxidation to reduce its tackiness or friction coefficient, thereby allowing for easier insertion of a person's finger into the opening 104. For example, subjecting a silicone-based inflatable elastic bladder to UV irradiation, corona, or plasma in combination with the introduction of polar groups into the surface region of the silicone may cause oxidation resulting in a vitrified silica-like surface layer. In other instances, the inflatable elastic bladder may be treated with a chemical coating, such as NuSil's R-2182 low coefficient of friction silicone coating, which may, when cured, offer such low tackiness and/or friction coefficient.

In some implementations, such as that shown in FIG. 3E (the other FIGS. 3A-3D, 3F, and 3G do not show this implementation), the housing 102 may be equipped with a stretchable textile-based cover or tube 107 that covers the inflatable elastic bladder and keeps it from directly contacting a person's skin during insertion and measurement. The cover may be made, for example, of a thin, stretchable woven material such as Lycra™ or Spandex™ so that it may stretch to accommodate expansion of the inflatable elastic bladder 110 without exerting too much compressive force on the inflatable elastic bladder 110.

In some implementations, the elastic material of the bladder 110 may be substantially transparent to permit light of certain wavelengths to pass through. Thus, optical sensors may be incorporated (e.g., within the inflatable elastic bladders 110) to perform additional functions with the finger blood pressure cuff 100. In some such implementations, a flexible printed circuit may be bonded or otherwise attached to a surface of the bladder 110 that defines, in part, the bladder volume. Such a circuit may include a photodetector and a photoemitter, for example, that form a photoplethysmographic (PPG) sensor. The photoemitter may be configured to direct light through the bladder 110 and into the dermis of the finger during a measurement, and the photoemitter may then measure the amount of this light that is diffusively reflected back out of the dermis and back through the bladder 110. The PPG sensor may otherwise operate in a manner typical of PPG sensors. In other such implementations, a transmissive PPG sensor may be used in which a photoemitter is positioned within the bladder volume on one side of the opening 104 and a photodetector is positioned within the bladder volume on another side of the opening 104 directly across or in a position therebetween. Even when a person's finger is inserted in the opening 104, the light that is emitted from the photoemitter may still, if bright enough, pass through the finger or at least a portion of the finger, thereby being modulated by the blood flow through the finger, and into the photodetector, where the detected signal may be used as an input for the PPG sensor. Such a PPG sensor may be configured to measure heart rate, blood oxygenation, SpO2 levels, and other cardiovascular parameters.

In some implementations, the inflatable elastic bladder 110 may include folds and other non-uniformities of varying flexibility that can serve to reduce pressure loss. For example, the inflatable elastic bladder 110 may include lobes as discussed above to reduce pressure loss.

In some implementations, the inflatable elastic bladder 110 may be molded from a single material. In other implementations, the inflatable elastic bladder 110 may be molded from more than one material.

A length (where length is measured along the axis along which the finger is inserted into the bladder 110) of the inflatable elastic bladder 110 may be sized based on a length of a user's finger. A longer inflatable elastic bladder 110 may provide improved arterial clamping. In some implementations, a length of the inflatable elastic bladder 110 may be between about 0.5 inches and about 1.5 inches or between about 0.75 inches and about 1.25 inches. In testing, a length of about 80% of the average adult phalange length was found to work well for a variety of adult test subjects with varying finger and hand sizes and still provide adequate arterial clamping and thus good blood pressure measurements.

In some implementations, a volume of the inflatable elastic bladder 110 when fully inflated may be between about 1 cubic centimeter and about 20 cubic centimeters or between about 3 cubic centimeters and about 10 cubic centimeters. This volume is significantly less than conventional inflatable bladders of conventional OBPM systems.

Figure 3G:
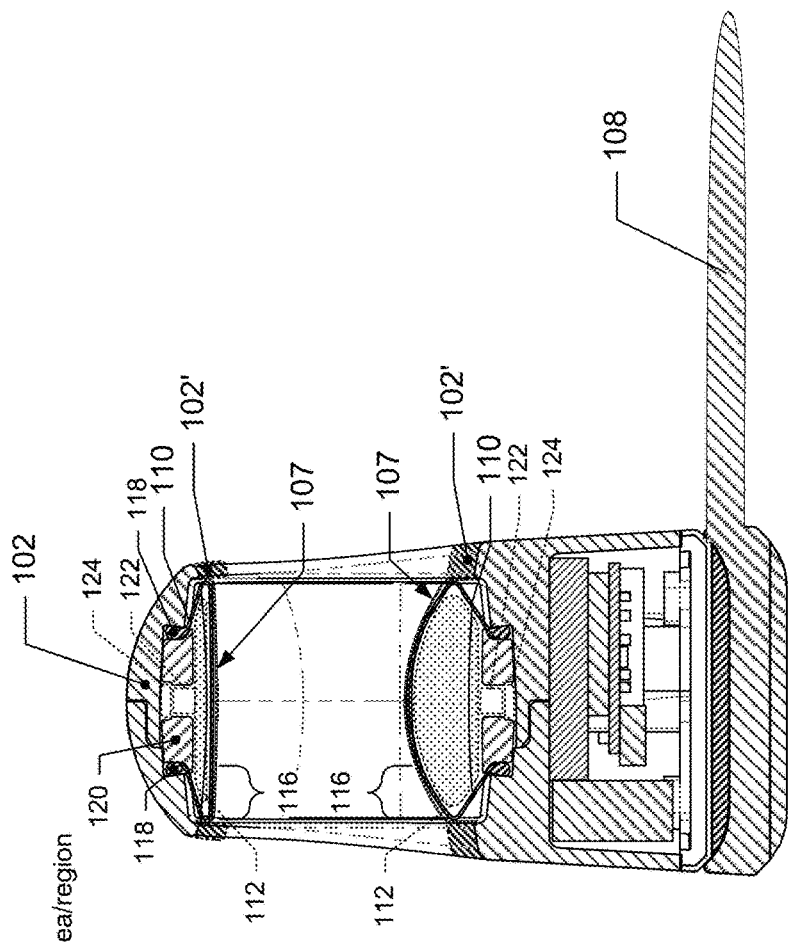
FIG. 3G shows a cross-sectional view of the finger blood pressure cuff through the section plane indicated in FIG. 3F.
Figure 3F:
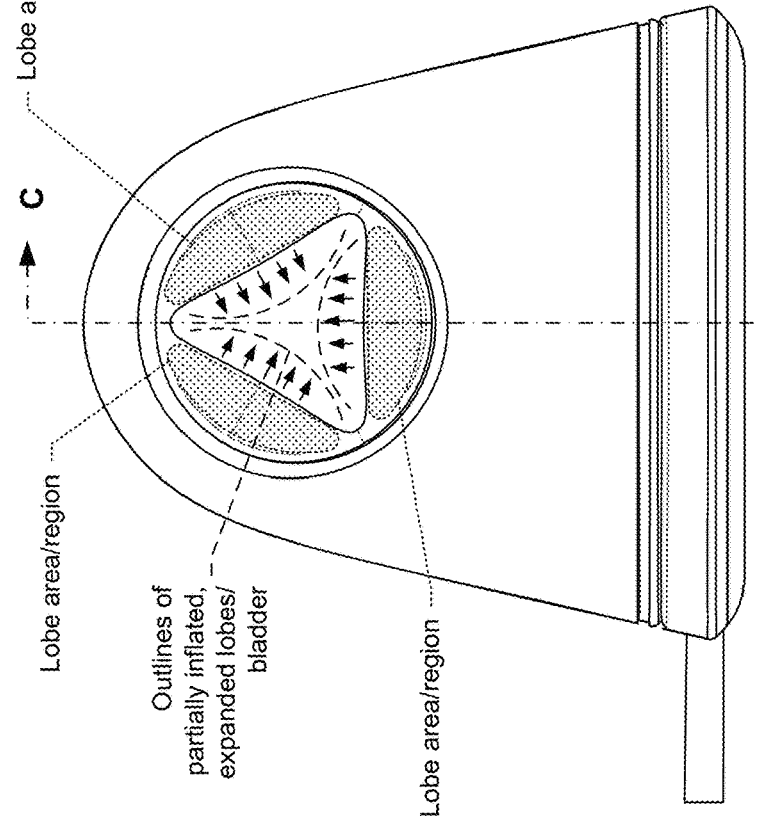
FIG. 3F shows a front view of the finger blood pressure cuff of FIG. 3A.

FIG. 3F shows a front view of the finger blood pressure cuff of FIG. 3A. FIG. 3G shows a cross-sectional side view of the finger blood pressure cuff of FIG. 3F cut along lines C-C. In FIG. 3G, the inflatable elastic bladder 110 further includes a pair of bellows 116, one at each end of the bladder 110. As used herein, "bellows" may refer to portions of the inflatable elastic bladder 110 that wrap, bend, or fold back from a remainder of the inflatable elastic bladder 110, e.g., from the membrane of the inflatable elastic bladder 110, to allow it to expand or contract. Here, the bellows 116 may be annularly disposed around the inflatable elastic bladder 110 and configured to reduce inflation resistance by allowing the bladder 110 to expand inwards towards the center of the opening 104 without requiring as much stretching of the bladder membrane. In FIG. 3F, a three-lobed bladder is shown, as well as arrows indicating how these lobes will inflate and dashed lines indicating the outlines of the lobes when in a pressurized state. Some implementations may have more than three lobes, e.g., four lobes, five lobes, and so forth. Some implementations may have less than three lobes, e.g., two lobes. As shown in FIG. 3G, the bellows 116 may be folded, bent, shaped, or conformed to reduce inflation resistance by the inflatable elastic bladder 110 during inflation. The bellows 116 may be disposed in the opening 104 of the housing 102 and attached to the housing 102 via one or more o-rings or seal beads 118 that are integral with the bladder 110, which may be compressed between the ring-shaped structure 120 and the housing 102 in order to clamp the bladder 110 to the ring-shaped structure 120 and form an airtight seal of a bladder volume or pressurizable volume 112. Thus, for example, the ring-shaped structure 120 may be thought of as having a first end and second end with a substantially cylindrical inner surface spanning between them (the surface may be cylindrical in overall shape but may, for example, have discontinuities, such as pressure ports, or be slightly elliptical or may have a non-regular shape that matches the cross-section profile of an average person's finger); the inflatable elastic bladder 110 may have a first seal bead and a second seal bead, each of which is sized and shaped so as to be able to be butted up against the first end and the second end, respectively. By compressing the first and second seal beads against the first and second ends of the ring-shaped structure 120, the inflatable elastic bladder 110 may be sealed to the ring-shaped structure 120, thereby forming the pressurizable volume or bladder volume 112. Also visible in FIG. 3G is an annular passage 124 that is provided between the ring-shaped structure 120 and the housing 102 and which provides a fluidic communication path between the holes/ports 122 that lead to the bladder volume 112 and the inlet/outlet ports 132, 142 for the pump 130 and/or pressure sensor 140.

In some implementations, the housing 102 may include a circumferential lip 102' (while the depicted implementation does not have such pronounced circumferential lips, the dotted outlines 102' indicate how such circumferential lips may appear) around the hole or opening 104 (if the hole is a through-hole, then the circumferential lip may optionally be on both sides of the hole; if a blind hole, then only on one side of the housing where the hole is). The circumferential lip may extend around the hole or opening 104 and may form an aperture smaller than the hole 104 (or at least, smaller than the hole or opening past where the circumferential lip is) and the lip may obscure some or all of the inflatable elastic bladder 110 from view when the finger blood pressure cuff is viewed along the center axis of the hole or opening 104 (and at least when the inflatable blood pressure cuff is at zero atmospheric gauge pressure). In some such implementations, the circumferential lip may obscure the fold of the bellows 116, e.g., the region where the bellows membrane transitions to the bellows 116, from view along the center axis. The circumferential lip may therefore help protect the inflatable elastic bladder 110 (in particular, the bellows fold) from abrasion or other wear and tear that may be caused by repeated insertion of a finger into the finger blood pressure cuff.

FIG. 4A shows an example inflatable elastic bladder 410 according to some implementations. This implementation of the inflatable elastic bladder 410 is axially symmetric about an axis, e.g., the center axis of the hole, and features a pair of bellows 416, as discussed above. The inflatable elastic bladder 410 includes a bladder membrane 411 for defining a bladder volume or pressurizable volume and further includes one or more seal beads 418 integral with the bladder membrane 411 and configured to attach to a housing of a finger blood pressure cuff. Such an inflatable elastic bladder 410 may be used to provide a pressurizable volume that has a continuous annular shape.

It is to be understood that the term "center axis," as used herein, is inclusive of axes that may not necessarily pass through the center of a particular structure or geometry, but that may be located in close proximity thereto (for example, if an opening is slightly asymmetric, the center axis may be a center axis that passes through a centroid of the opening, or it may pass through a center of a circle that circumscribes the opening). Generally speaking, however, the center axis of a structure or feature may be located within a first distance of a "true" center axis of the structure or feature, e.g., a center axis passing through a centroid or that forms an axis of symmetry of that structure or feature. The first distance may, for example, be ±10% of the largest dimension of the feature defining the center axis. For example, if the opening is generally circular but not actually circular, the center axis may pass through a point within ±10% of the largest dimension of the opening from the opening's centroid.

FIG. 4B shows another example inflatable elastic bladder 420 according to some other implementations. The inflatable elastic bladder 420 of FIG. 4B is identical to that of FIG. 4A except that this bladder 420 also includes a plurality, e.g., four, longitudinal ribs 421, which may be included to provide some stiffness to the bladder 420 and potentially encourage folds/pleats in the bladder 420 to form at predetermined locations. The longitudinal ribs 421 may extend along directions parallel to the center axis of the hole (or the axis of axial or radial symmetry of the inflatable elastic bladder) and may be arranged in a circular array centered on the center axis. Each of the inflatable elastic bladders 410, 420 in FIGS. 4A and 4B depict inflatable elastic bladders with an axially uniform annular inflatable volume.

FIG. 5A shows an example inflatable elastic bladder 510 with three inflatable lobes 511 according to some implementations. It is important to understand that the shape that is depicted in the example depicted in FIG. 5A is the shape of the example bladder 510 at rest, i.e., not subject to pressurization (thus, for example, the shape of the bladder when at zero gauge pressure—the pressure within the bladder being equalized with the ambient atmospheric pressure outside of the bladder). Thus, the as-molded shape of the bladder 510 of FIG. 5A includes the lobe features that are visible. When this bladder 510 is pressurized, the lobes 511 will expand inwards, starting with the points that are already closest to the center, thereby applying pressure to the finger at generally equally-spaced locations around the circumference of the finger.

FIG. 5B shows an example inflatable elastic bladder 520 with three helically twisted lobes 521 according to some implementations. The helical twist in the lobes 521 may be included to cause creases to form between the lobes 521 to follow helical paths instead of paths that are generally aligned with the finger bones/center axis of the bladder 520. As can be seen in cross-sections J-J through M-M, the triangular opening in the middle of the membrane experiences a helical twist through about 40° (as shown by the dash-dot-dash reference axis in those Figures) along the length of the bladder 520. This reduces the chance that larger arteries in the finger, which generally extend in directions aligned with the finger bones, may align with one of the creases and therefore not be subjected to as much clamping pressure as the regions of the finger that are in contact with the middles of the lobes 521.

FIG. 5C shows an example inflatable elastic bladder 530 with centering lobes 531 that extend further towards the center of the opening as compared with the tri-lobe design of FIG. 5A so that a finger that is inserted will be more aggressively "centered" by the lobes 531 according to some implementations.

Each of FIGS. 5A-5C show a perspective view, a front view, and a cross-sectional view based on a cutaway of the front view. FIG. 5B further shows a side view of the inflatable elastic bladder 520 with helically twisted lobes 521, with multiple cross-sectional views cut from along lines J-J, K-K, L-L, and M-M for depicting the twisted lobes 521.

In some implementations, introducing multiple lobes 511 in the inflatable elastic bladder 510 as shown in FIG. 5A may improve conformance of the inflatable elastic bladder 510 on various finger sizes. In some implementations, introducing twisted lobes 521 in an inflatable elastic bladder 520 as shown in FIG. 5B may improve arterial clamping and further reduce pressure loss. In some implementations, using centering lobes 531 in the inflatable elastic bladder 530 as shown in FIG. 5C, or pre-inflating the lobes so that they appear similar to those in FIG. 5A, may provide benefits, such as improved contact with a user's finger during insertion, and thus further reduce pressure loss.

Typical OBPM systems do not inflate an inflatable bladder until a blood pressure measurement is initiated. However, the finger blood pressure cuff of the present disclosure may include a pre-inflation mechanism, e.g., maintaining a slight amount of pressurization in the bladder sufficient to distend the bladder into a configuration similar to the elastic bladder as shown in FIG. 5C prior to further inflating the elastic bladder for a blood pressure measurement. The elastic bladder may occupy a desired volume, e.g., a partially inflated volume such as shown in FIG. 3F, in the opening prior to initiation of a blood pressure measurement. A pre-inflated elastic bladder may reduce pressure loss that may result from inflating the elastic bladder to a certain volume to gain contact with a user's finger. A pre-inflated elastic bladder may contact or nearly contact a user's finger positioned in the opening regardless of whether the user's finger is small or large. Pre-inflation reduces the volume requirement of inflating the elastic bladder to obtain contact with the user's finger. Whereas conventional OBPM systems may require wrapping and cinching an inflatable bladder around a user's appendage to obtain "tight" or "snug" contact, a pre-inflated elastic bladder introduces volume in the bladder to obtain contact without changing the diameter of the opening or outer diameter of the bladder.

In some implementations, the finger blood pressure cuffs of the present disclosure may include a controller that is configured to control the pump to pre-inflate the inflatable elastic bladder from a first pressure, e.g., atmospheric pressure, to a second pre-measurement pressure or second pressure, as discussed above, prior to insertion of a finger. Upon insertion of a finger, the controller may cause the pump to further inflate the inflatable elastic bladder to a third pressure at which the pressure sensor detects pulsatile variations in the pressure, e.g., pulsatile variations in line with those caused by heartbeats (for example, those with a periodicity of between about 50 cycles per minute and 200 cycles per minute) and then to a fourth pressure at which the pulsatile variations in the pressure decrease to a first predetermined level, e.g., 0 or less than 5% of the maximum pulsatile variations observed. Alternatively, the controller may cause the pump to pressurize the inflatable elastic bladder to the fourth pressure after reaching the second pressure, e.g., by pressurizing the inflatable elastic bladder to a pressure that is higher than the maximum expected measurement pressure and then allowing the pressure to decrease in a controlled manner until pulsatile variations in the pressure signal are detectable. In such implementations, the pressure may then be allowed to further decrease in a controlled manner to reach the third pressure.

Figure 6A:
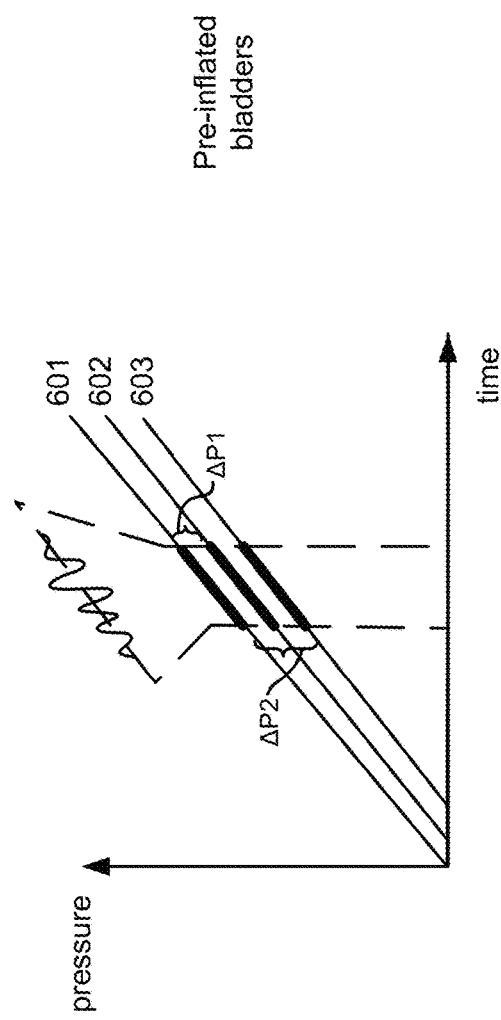
FIGS. 6A and 6B show graphs of inflation profiles for a pre-inflated elastic bladder and for an elastic bladder that is not pre-inflated.
Figure 6B:
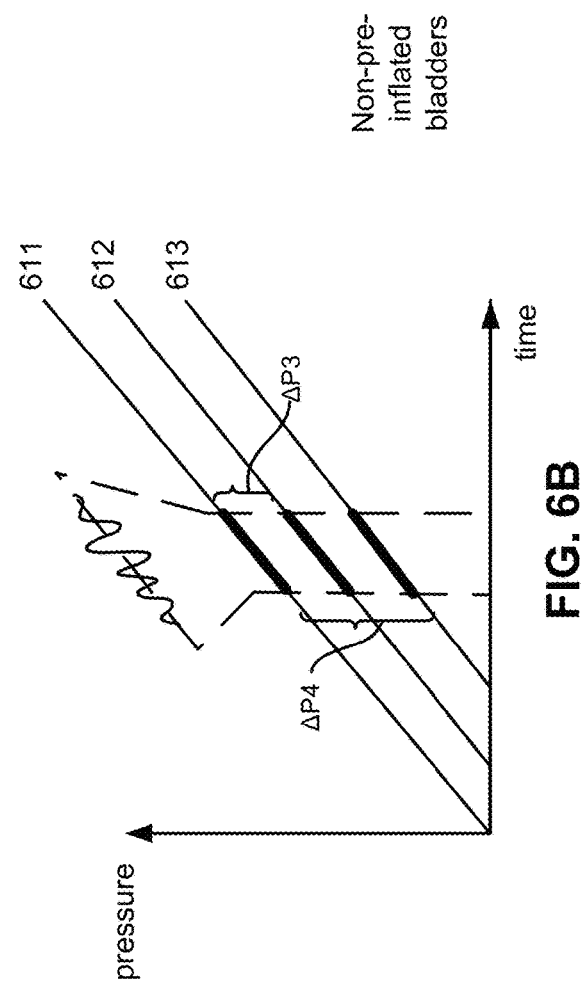

FIGS. 6A and 6B compare inflation profiles (pressure profile during inflation) between pre-inflated bladders and non-pre-inflated bladders. FIG. 6A depicts inflation profiles for pre-inflated bladders and FIG. 6B depicts inflation profiles for non-pre-inflated bladders. Each of FIGS. 6A and 6B depict inflation profiles for (1) a pressure sensed by the pressure sensor (depicted by pressure 601, 611), (2) an actual applied pressure on a medium-sized finger (depicted by pressure 602, 612), and (3) an actual applied pressure on a small-sized finger (depicted by pressure 603, 613). The pressures where one or more pulses are recorded are used to estimate blood pressure. The one or more pulses in the inflation profile may be part of oscillometric data for estimating a user's blood pressure. In FIG. 6A for pre-inflated bladders, at a given time when the one or more pulses are recorded, a first pressure difference between the observed pressure 601 and the actual applied pressure 602 on a medium-sized finger is represented by $\Delta P_1$, and a second pressure difference between the observed pressure 601 and the actual applied pressure 603 on a small-sized finger is represented by $\Delta P_2$. In FIG. 6B for non-pre-inflated bladders, at a given time when the one or more pulses are recorded, a third pressure difference between the observed pressure 611 and the actual applied pressure 612 on a medium-sized finger is represented by $\Delta P_3$, and a fourth pressure difference between the observed pressure 611 and the actual applied pressure 613 on a small-sized finger is represented by $\Delta P_4$. FIGS. 6A and 6B show that with pre-inflated bladders, the actual applied pressure 602, 603 is closer to the observed pressure 601 and varies less with different finger sizes. Therefore, the final estimation of blood pressure will generally be more accurate. With non-pre-inflated bladders, the actual applied pressure 612, 613 is significantly less than the observed pressure 611 and is even more significant for smaller finger sizes.

Pump Control of the Blood Pressure Cuff

A pressurizing pump may be used to control inflation/deflation of an inflatable bladder of a blood pressure cuff. The pressurizing pump may be fluidically connected to the pressurizable volume of inflatable bladder, where the pressurizing pump is configured to pressurize the pressurizable volume and cause the inflatable bladder to inflate and contact a user's appendage (e.g., a user's finger) when the pressurizing pump is activated. When the pump is activated, the pressurizable volume is inflated and expands towards the user's appendage to contact the user's appendage under the driving of the pressurizing pump. A blood pressure measurement may occur when a user's appendage is inserted in an opening of the blood pressure cuff and the pump is activated to pressurize the pressurizable volume and contact the user's appendage. The blood pressure cuff may include a pressure sensor for generating pressure data indicative of pressure in the pressurizable volume as a function of time, where the pressure data can be used to obtain blood pressure measurements of the user.

In some implementations, the pressurizing pump may be a piezoelectric pump. Typical piezoelectric pumps for controlling inflation may pressurize an elastic bladder too quickly for detecting a pulse wave in a blood pressure measurement. For example, a typical pump may pressurize the elastic bladder at an inflation rate of greater than 20 mmHg per second, greater than 50 mmHg per second, greater than 80 mmHg per second, or greater than 100 mmHg per second. Such high inflation rates are too fast for pressurizing a volume around a user's finger. Then, a pulse wave in a blood pressure measurement is not detected. However, the blood pressure cuff of the present disclosure includes a pump and control hardware that controls the inflation rate to allow for detection of a pulse wave in a blood pressure measurement. In some implementations, the inflation rate (or, more accurately, the pressurization rate) of the pump is less than about 20 mmHg per second, less than about 10 mmHg per second, or less than about 5 mmHg per second. For example, the inflation rate of the pump can be controlled to be between about 1 mmHg and about 10 mmHg per second. Furthermore, the inflation rate of the pump may be modulated to maintain a linear or near-linear pressure-time history for the bladder pressure, excluding any non-linearities from the oscillometric waveform. For example, the pressure rise in the bladder can be maintained to be approximately linear at an inflation rate between about 1 mmHg per second and about 10 mmHg per second, such as about 4 mmHg per second.

The blood pressure cuff of the present disclosure may include a controller or control unit coupled with the pump. The control unit or controller may include at least one of a general purpose single- or multi-chip processor, a digital signal processor, an application specific integrated circuit, a field programmable gate array or other programmable logic device, discrete gate or transistor logic, or discrete hardware components. In some embodiments, the controller may be capable of controlling the pump according to instructions (e.g., software) stored on one or more non-transitory computer-readable media. Such non-transitory media may include the memory of the blood pressure cuff. The controller is configured to input control signals to drive the pump according to various parameters.

Additional control hardware may be coupled with the controller for controlling various operations of the pump or, more generally, the blood pressure cuff. The controller may be coupled with, for example, a DC-DC booster circuit for varying a drive voltage of the pump. The controller may optionally be coupled with an exhaust valve for deflating and contracting the pressurizable volume of the inflatable bladder. For example, in some implementations (such as that depicted in FIG. 3E; the FIGS. 3A-3D, 3F, and 3G do not depict these additional features), a valve 105 may be fluidically connected with the pressurizable volume, e.g., via the annular passage 124. The valve 105 may, for example, be a controllable valve operated by the controller or may be a mechanical pop-off valve that automatically allows pressure beyond a pre-set point, e.g., 275 mmHg to 300 mmHg gauge pressure, to be bled off. In the case of a controllable valve 105, the controller may monitor the data from the pressure sensor may cause the valve 105 to release pressure that exceeds a preset threshold, e.g., 275 mmHg to 300 mmHg gauge pressure. In some implementations, the housing 102 may also or alternatively include a mechanical plug 103 that may be accessible by a user from the exterior of the device; the mechanical plug 103 may be configured to be easily removable by a user in the event that the pressure within the inflatable elastic bladder 110 exceeds a comfortable amount (and/or if there is a malfunction that prevents the pump from turning off, for example).

The blood pressure cuff of the present disclosure includes the controller for varying one or more parameters to influence the inflation rate of the pump. The parameters for controlling the inflation rate may be fixed during a blood pressure measurement or may be continuously varied during the blood pressure measurement. By way of an example, a rate of change of a duty cycle may be fixed during a blood pressure measurement, e.g., set according to a preset sequence of duty cycle lengths, or the rate of change of a duty cycle may dynamically change based at least in part on pressure readings from the blood pressure measurement, e.g., the duty cycle length may be varied based on feedback from a pressure sensor.

The controller may be configured to control at least one of a duty cycle, voltage, or drive frequency of the pump. Controlling one or more of the aforementioned characteristics of the pump may control an inflation rate of the pump.

Figure 7:
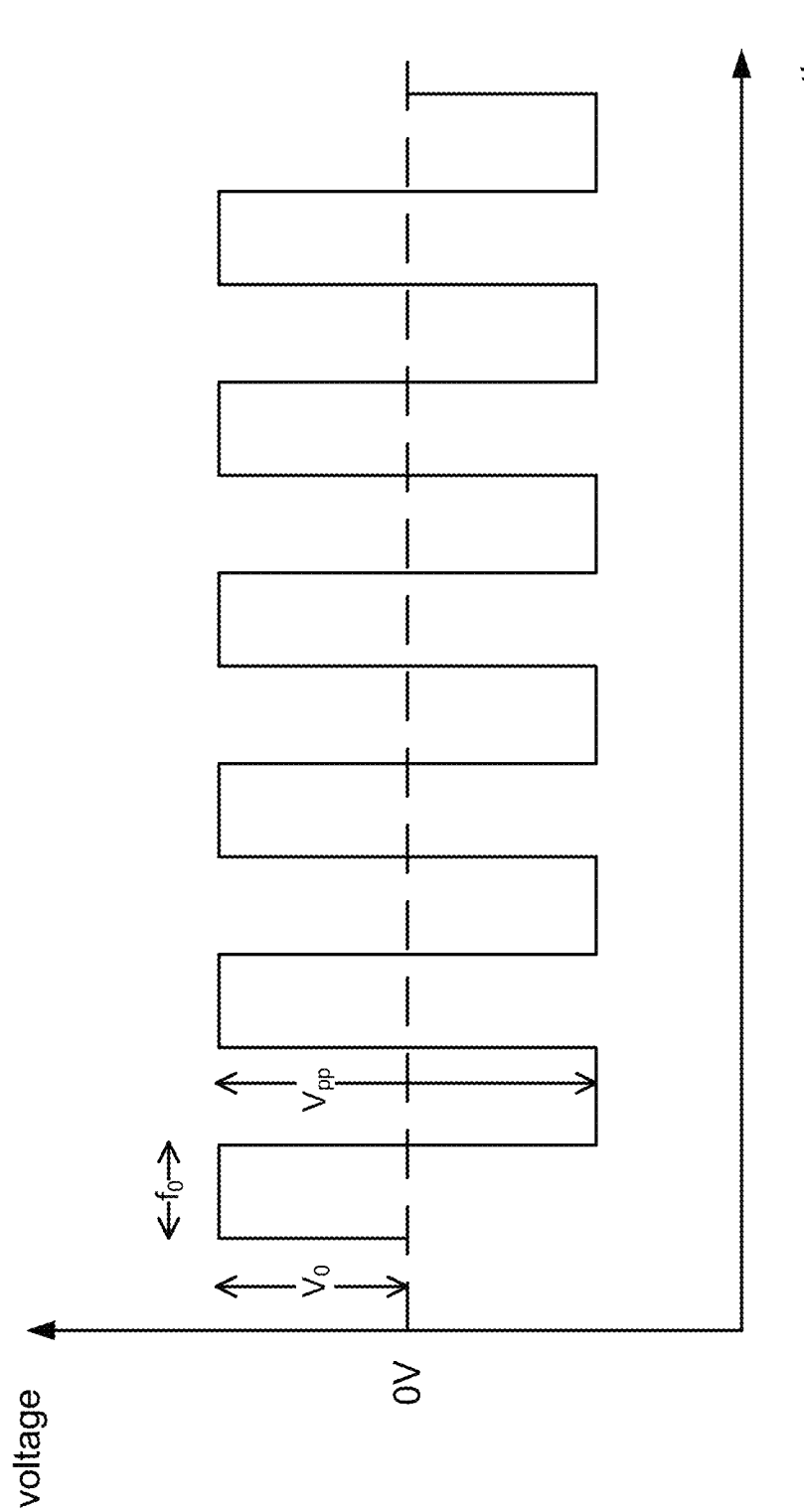
FIG. 7 shows a graph of a typical waveform for a piezoelectric pump.

A piezoelectric pump generally discharges air at a flow rate when in response to alternating drive signals when an AC current is applied. Typical piezoelectric pumps are engineered to operate a response to alternating driving signals of a particular frequency and voltage, e.g., a square wave signal having a nominally constant frequency and voltage. It will be understood that a sine wave signal may be applied, a square wave signal may be applied, and so on. As shown in FIG. 7, a typical piezoelectric pump may be operated using a square waveform signal though it will be understood that other piezoelectric pumps may be operated using a sine wave signal or other alternating driving signal. The alternative driving signal may be characterized by an amplitude $V_0$ and a drive frequency $f_0$. An inflation rate of the pump may be determined at least in part by controlling characteristics such as the amplitude and drive frequency of the pump. A peak-to-peak voltage $V_{pp}$ may be used when discussing the value of the voltage applied to the pump, where the amplitude $V_0$ is half the value of the peak-to-peak voltage $V_{pp}$. A drive frequency of the signal can be, for example, 23 kHz, and a driving voltage can be, for example, 5-30 $V_{pp}$.

Though the drive frequency cannot generally be adjusted, there may be some ability to adjust within the design limits of the driving signal. Accordingly, in some implementations, the drive frequency of the pump may be adjusted to control the pump speed, thereby controlling its inflation rate. However, dropping the drive frequency below the engineered lower limit of acceptable driving signal frequencies may cause the pump to no longer operate correctly, and it may be unable to adequately provide any pressurization. Nonetheless, in some embodiments, the controller coupled to the pump may be configured to modify the drive frequency to change the inflation rate of the pump. In some embodiments, the drive frequency of the pump is equal to or greater than about 23 kHz. The drive frequency of the pump may be modified to be outside audible noise.

In addition or in the alternative, the inflation rate of the piezoelectric pump can be controlled by controlling the voltage of the pump. Also referred to as "amplitude modulation," the voltage applied to the pump may be controlled within a given desired amplitude range. In some embodiments, the voltage applied to the pump may increase within the desired amplitude range. If the peak-to-peak potential difference $V_{pp}$ goes from about 12 $V_{pp}$ to about 40 $V_{pp}$, then the amplitude range is from about 6 V to about 20 V. A higher voltage or amplitude generally corresponds to a larger volume displacement with a piezoelectric pump. In some embodiments, the controller may be configured to increase the peak-to-peak voltage of the pump from a first peak-to-peak voltage to a second peak-to-peak voltage at a selected rate. By way of an example, the first peak-to-peak voltage may be between about 5 $V_{pp}$ and about 20 $V_{pp}$ (e.g., 10 $V_{pp}$) and the second peak-to-peak voltage may be between about 40 $V_{pp}$ and about 80 $V_{pp}$ (e.g., 60 $V_{pp}$), which corresponds to an amplitude range of 2.5-10 V (e.g., 5 V) to 20-40 V (e.g., 30 V). The amplitude may gradually increase according to a selected rate. In some embodiments, the amplitude increases at a selected rate between about 2 V per second and about 10 V per second, such as about 5 V per second. Changing the amplitude of the driving signal may result in a change in the amount of noise heard from the pump. In some implementations, amplitude modulation may reduce noise emanating from the piezoelectric pump.

In addition or in the alternative, the inflation rate of the pump may be controlled by controlling the duty cycle of the pump. A duty cycle can refer to the percentage of on time ($T_{on}$) during the total of on time and off time, where $T=T_{on}+T_{off}$ in a given cycle. The duty cycle can gradually increase at a selected rate to reach a desired duty cycle. In some implementations, the selected rate may be fixed during a blood pressure measurement, and a duty cycle may increase from a first duty cycle (e.g., less than 100% duty cycle) to a second duty cycle (e.g., 100% duty cycle) at a selected rate. In some implementations, a selected rate may be between about 0.1% and about 20% increase in duty cycle per second. By way of an example, the duty cycle may increase from 40% duty cycle to 100% duty cycle at a rate of about 1% increase in duty cycle per second.

In some implementations, the selected rate may dynamically change during a blood pressure measurement, and a duty cycle may increase from a first duty cycle (e.g., less than 100% duty cycle) to a second duty cycle (e.g., greater than the first duty cycle) at a first rate, and a duty cycle may increase from the second duty cycle to a third duty cycle (e.g., greater than the second duty cycle) at a second rate. The first rate is different than the second rate, where each of the first and second rates is between about 0.1% and about 20% increase in duty cycle per second. By way of an example, the duty cycle may increase from 20% duty cycle to 30% duty cycle at a rate of about 1% increase in duty cycle per second, and the duty cycle may subsequently increase from 30% duty cycle to 50% duty cycle at a rate of about 5% increase in duty cycle per second. The duty cycle may increase until 100% duty cycle is reached or, in some cases, until a lower level of duty cycle is reached.

Figure 8:
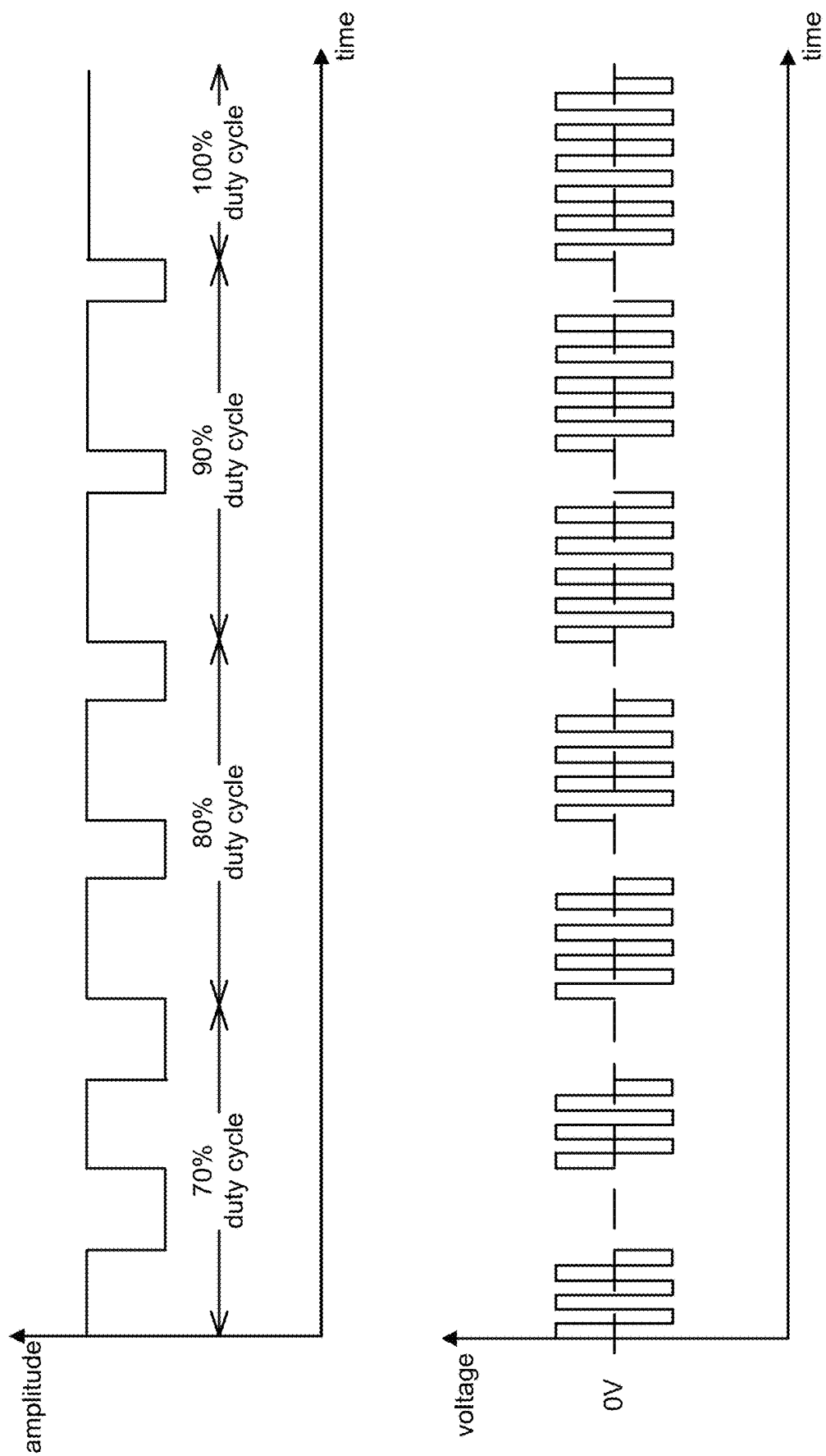
FIG. 8 shows a diagram of voltage as a function of time with a gradually changing duty cycle of the square waveform signal driving a piezoelectric pump.

FIG. 8 shows a diagram of voltage as a function of time with a gradually changing duty cycle of the square waveform signal driving a piezoelectric pump. To be clear, the duty cycle signal is used to modulate the fixed-frequency driving signal for the pump; when the duty cycle signal is 100%, the fixed-frequency driving signal is provided to the pump. When the duty cycle signal is 0%, the fixed-frequency driving signal is not provided to the pump. Thus, the pump is driven at a constant frequency during the intervals of the duty cycle where the duty cycle phase is "on", and during the duty cycle "off" phase the pump is not driven In FIG. 8, the piezoelectric pump is being driven by a duty cycle signal with a pulse wave frequency of about 5000 Hz. As shown in FIG. 8, the duty cycle gradually increases from 70% duty cycle to 100% duty cycle at a rate of 10% increase in duty cycle per second. Whereas the square waveform signal in FIG. 7 is continuous, the square waveform signal in FIG. 8 is discontinuous or "chopped up." This causes, as noted above, the piezoelectric pump to operate intermittently and inflate the bladder at a slower inflation rate instead of at full speed. Such a slower inflation rate may be suitable for inflating smaller volumes.

As discussed below, the controller may be further coupled with a pressure sensor in fluidic communication with the inflatable bladder and configured to produce pressure data indicative of pressure within the pressurizable volume as a function of time. In some implementations, the controller is configured to change the increase in the duty cycle from the first rate to the second rate when a pressure within the pressurizable volume reaches a threshold pressure. This allows the increase in the duty cycle to slow down or speed up when certain pressure levels are reached, thereby controlling the inflation rate of the pump. For example, the first rate may be 1% increase per second and the second rate may be 0.5% increase per second, or vice versa. In some implementations, the threshold pressure may be a pressure between about 50 mmHg and about 250 mmHg, or between about 100 mmHg and about 180 mmHg. In some implementations, the controller is configured to dynamically change the duty cycle of the pump based at least in part on the pressure data of the pressurizable volume. Certain duty cycles may not be powerful enough to pressurize the pressurizable volume past certain pressure levels, and so duty cycles may be dynamically tuned based on the pressure data.

Figure 9:
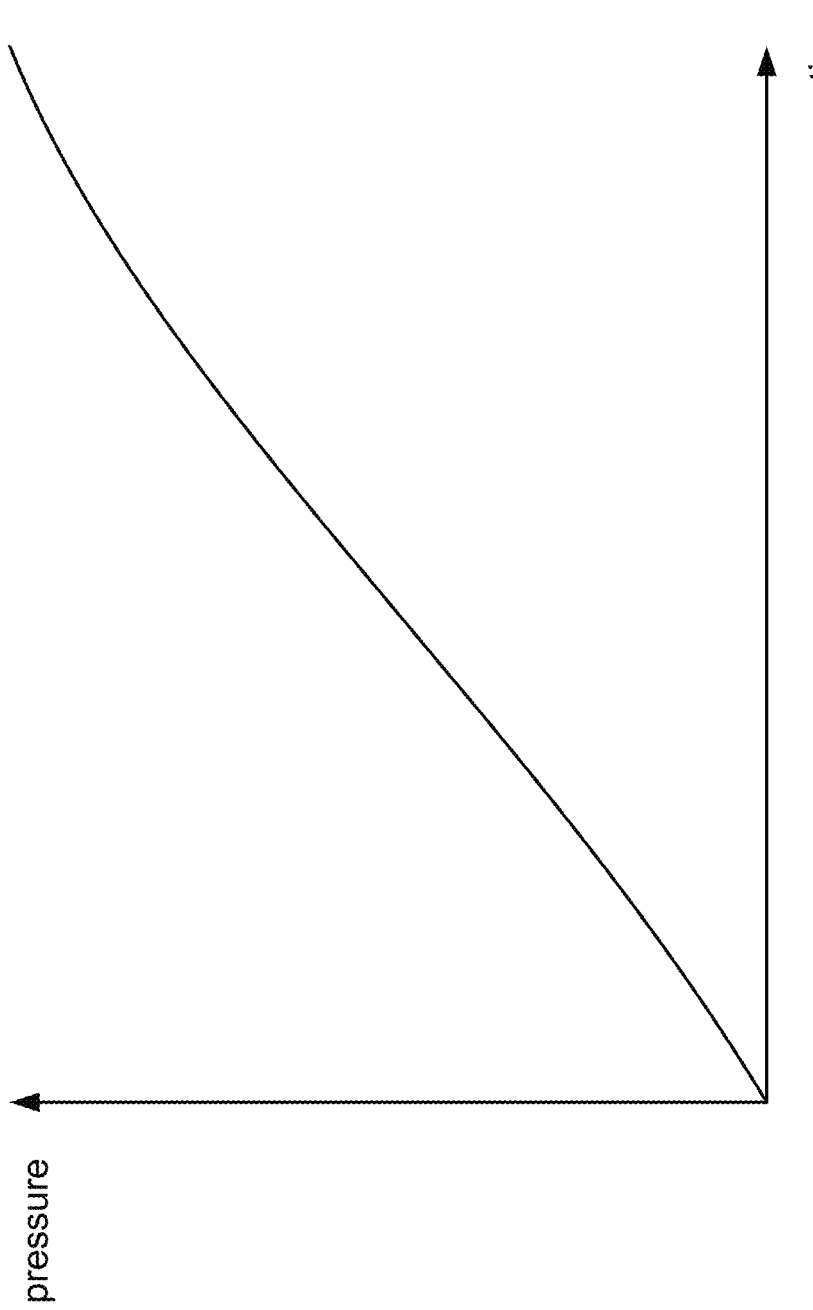
FIG. 9 shows an inflation profile of a finger blood pressure cuff using a piezoelectric pump.

Modifying the duty cycle of the pump may cause the distortions in the linearity of the inflation profile, which may interfere with accurate reading and recording of pulse information in a blood pressure measurement. Accordingly, controlling the duty cycle and the selected rate of change of the duty cycle may be optimized to achieve a linear or substantially linear inflation profile. In other words, the duty cycle may be gradually increased at a desired rate so that the inflation profile is substantially linear. FIG. 9 shows an inflation profile of a finger blood pressure cuff using a piezoelectric pump. As shown in FIG. 9, the inflation rate of the inflation profile is approximately linear. By way of an example, increasing the duty cycle from 20% to 40% at 1% increase per second followed by increasing the duty cycle from 40% to 60% at 0.5% increase per 0.1 seconds may achieve a substantially linear inflation profile.

A controller of the piezoelectric pump has adjusted one or more of a duty cycle, voltage, and drive frequency of the piezoelectric pump to control the inflation rate of the piezoelectric pump. Not only does adjusting parameters such as duty cycle, voltage, and/or drive frequency reduce the inflation rate of the piezoelectric pump, but the inflation rate may be more linear.

Pressure Profile and Measurements of the Blood Pressure Cuff

OBPM systems measure a user's blood pressure by observing and analyzing oscillometric patterns in a pressure profile. In conventional OBPM systems, the pressure profile is obtained by inflation of a blood pressure cuff to a desired pressure to at least temporarily occlude blood flow in an underlying blood vessel, which is then followed by deflation of the blood pressure cuff, with the cuff pressure being noted when the heartbeat is first registered again (for systolic pressure) and when the heartbeat ceases to be registered (for diastolic pressure). A typical blood pressure measurement may inflate to an initial pressure greater than the systolic blood pressure and then deflate to a final pressure below the diastolic blood pressure. During the blood pressure measurement, a pressure profile may be recorded including one or more pulses that occur during inflation and deflation. The pulses are caused by the user's heartbeats. Techniques known in the art for determining blood pressure from the one or more pulses recorded in a pressure profile can be used.

In the present disclosure, a blood pressure cuff such as a finger blood pressure cuff may be inflated in a first pressure profile to an initial pressure at least slightly above systolic pressure. At some point during inflation, the bladder and the dermis will come into contact with enough pressure that pulsations of blood in the dermis will be transmitted to the bladder and evident as pressure pulsations measurable by the pressure sensor. These pulsations will generally increase in strength as the dermis and bladder are pressed more firmly together, resulting in better coupling between the dermis and the bladder, up until the point when the bladder exerts so much pressure through the dermis to the artery that blood flow stops (at which point the pulsations will also cease. Generally speaking, the pressure at which pulsations in the dermis are first detectable by the pressure sensor have a correlation to the person's diastolic blood pressure, whereas the higher pressure at which blood flow stops and the pulsations end generally have a correlation to the person's systolic blood pressure. More particularly, typical oscillometric measurements may use the first and last pulsations of a specific amplitude normalized to its maximum to ascertain measurements for diastolic and systolic blood pressure. Thus, a measurement may typically involve inflating the cuff to a pressure above the systolic pressure and logging the pressure data that is measured during such pressurization. The systolic pressure may then be estimated from information derived from the pressure data obtained during inflation. The diastolic pressure may be estimated from information derived from the pressure data obtained during deflation.

The blood pressure cuff of the present disclosure may more reliably and accurately determine a person's blood pressure, including systolic and diastolic pressure, by causing the pump to pressurize a pressurizable volume of an inflatable bladder to a first pressure greater than a maximum amplitude pressure in a first pressure profile, and then subsequently causing the pump to maintain the pressurizable volume at a second pressure for a duration in a second pressure profile, where the second pressure is based at least in part on information from the first pressure profile. The blood pressure cuff may include a controller coupled to a pump in fluidic communication with the inflatable bladder, and coupled to a pressure sensor in fluidic communication with the inflatable bladder. The inflatable bladder defines, at least in part, the pressurizable volume. The pump is configured to pressurize the pressurizable volume and cause the inflatable bladder to contact a user's appendage when the pump is activated. The pressure sensor is configured to obtain and produce pressure data indicative of pressure within the pressurizable volume as a function of time, where the pressure data includes oscillometric data in the first pressure profile and pulse information in the second pressure profile. The first pressure profile may be indicative of the pressure within the pressurizable volume up to the first pressure as a function of time, and the second pressure profile may be indicative of the pressure within the pressurizable volume as a function of time after reaching the first pressure. In some embodiments, the second pressure profile is indicative of the pressure within the pressurizable volume when the pressurizable volume is maintained at the second pressure.

In order to obtain a cleaner signal and a more reliable estimate of a person's blood pressure, in some implementations, the first pressure profile may be approximately linear at a specific rate, such as between about 1 mmHg per second and about 10 mmHg per second. In some implementations, the first pressure profile may be non-linear, where the first pressure profile may be slower when approaching systolic pressure and diastolic pressure based on sensing pressure fluctuations. In some implementations, the first inflation profile may include a stepped and/or slower inflation profile, where the stepped and/or slower inflation profile may measure one or more of pulse wave analysis (PWA) features, arterial compliance, respiration, atrial fibrillation, and other physiological metrics.

Figure 10:
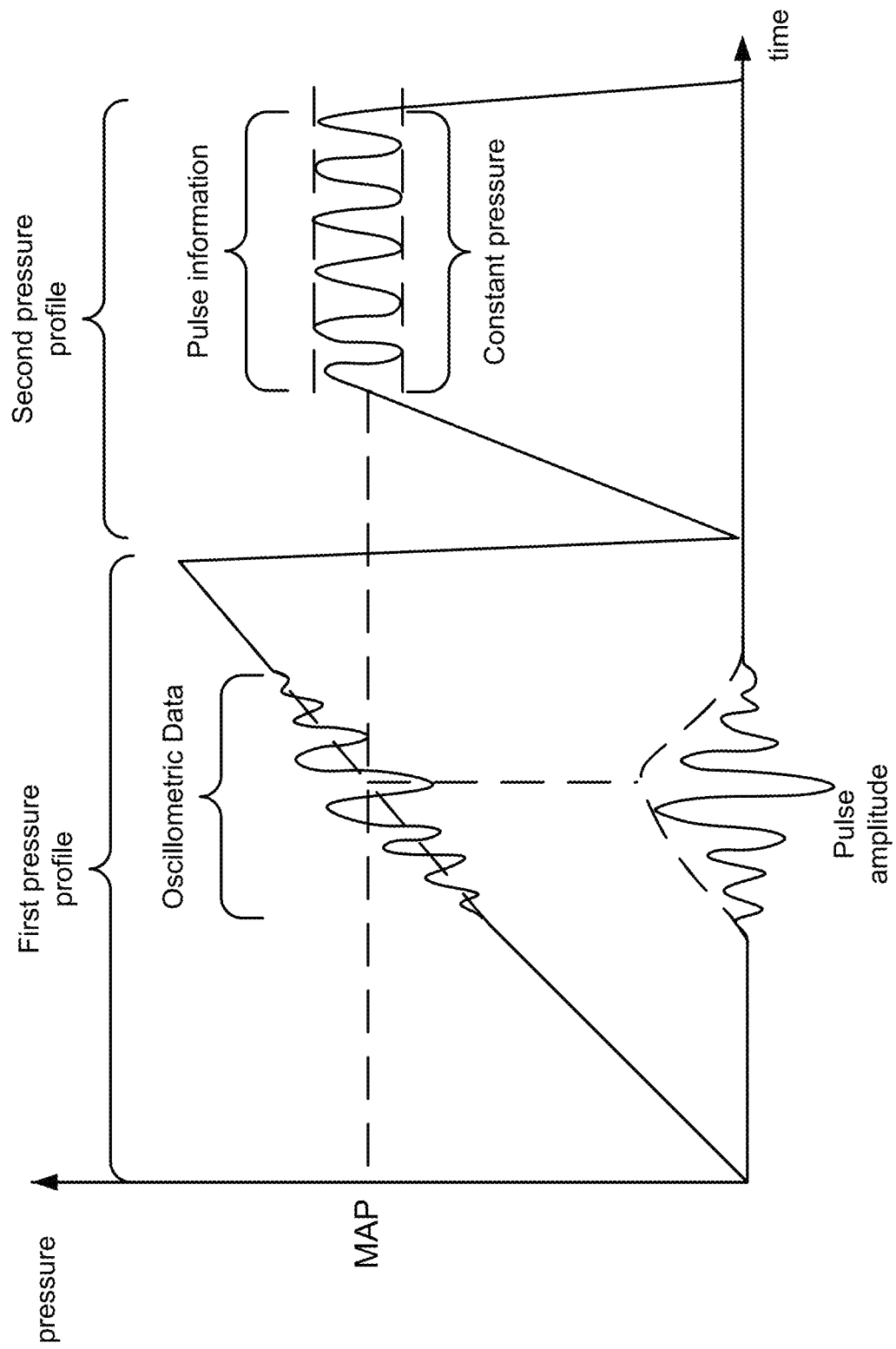
FIG. 10 shows a graph for a blood pressure measurement depicting a first pressure profile followed by a second pressure profile, where the second pressure profile inflates to a targeted pressure and is held at the targeted pressure.
Figure 11:
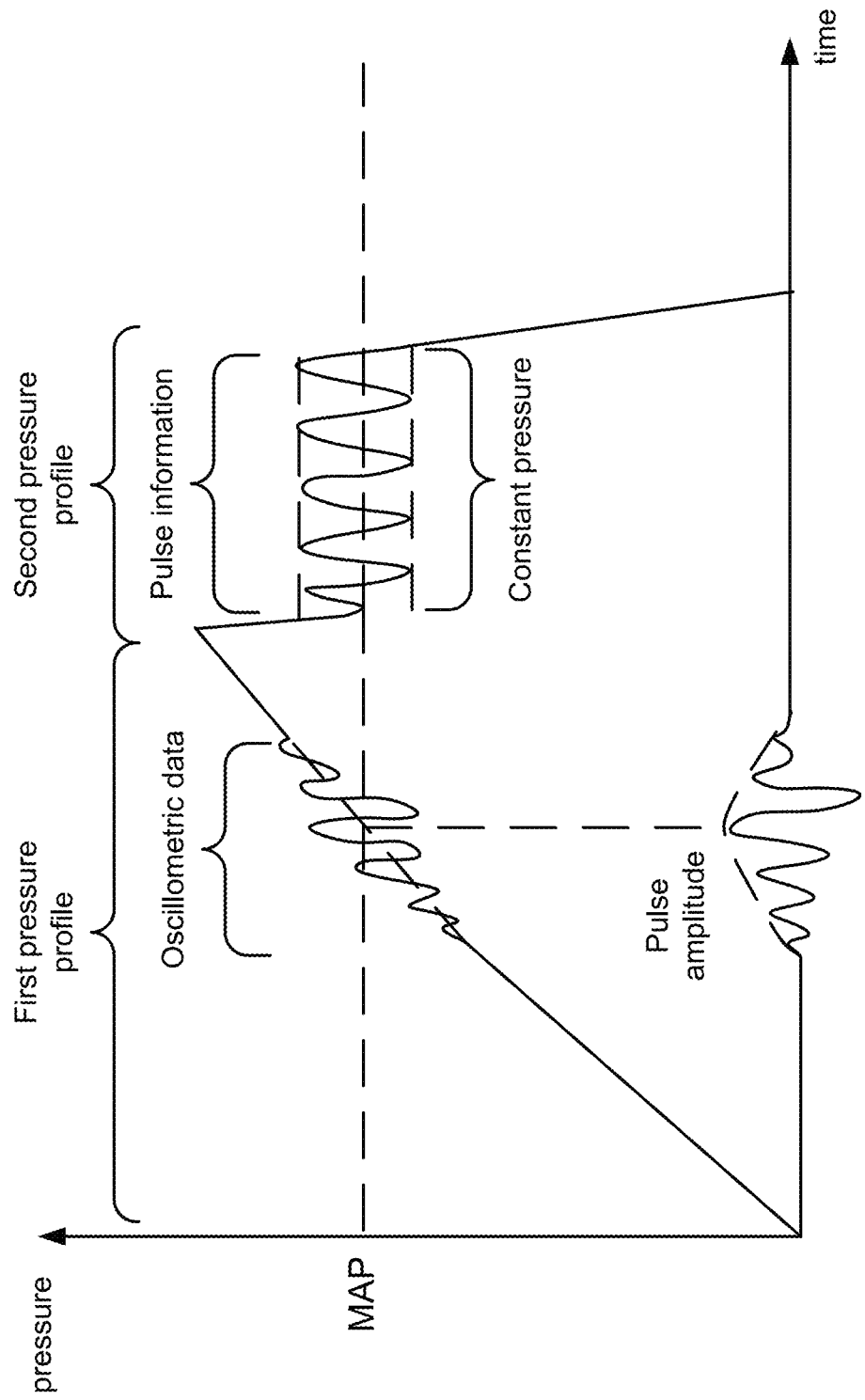
FIG. 11 shows a graph for a blood pressure measurement depicting a first pressure profile followed by a second pressure profile, where the second pressure profile deflates to a targeted pressure and is held at the targeted pressure.

In the present disclosure, the blood pressure cuff may undergo a process to record pressure data during inflation/deflation to a second pressure profile subsequent to the first pressure profile. In the second pressure profile, the blood pressure cuff may deflate from the first pressure to zero gauge pressure or other lower pressure and then re-inflate to a second pressure as shown in FIG. 10. Alternatively, the blood pressure cuff may deflate from the first pressure to a second pressure as shown in FIG. 11. During the second pressure profile, the bladder may be maintained at the second pressure for a sufficient duration to record multiple oscillations or pulsations originating from pulsative behavior in the user's blood vessels. In some implementations, the applied pressure may be held at the second pressure for a duration between about 1 second and about 15 seconds, between about 3 seconds and about 10 seconds, or between about 5 seconds and about 10 seconds. The second pressure for the second pressure profile may be obtained from information in the first pressure profile. For example, the second pressure can be a maximum amplitude pressure from oscillometric data (the oscillometric data referring to the oscillatory data that is produced in the first pressure profile due to the pulsations in the subject's blood vessels). Rather than continuously deflating or inflating past the second pressure after a first inflation process, the second inflation/deflation process can hold the applied pressure at the second pressure to obtain pulse information in the second pressure profile. Pulse information may be used to extract and characterize one or more of PWA features, arterial compliance, respiration, atrial fibrillation, and other physiological metrics. Since the pressure is consistent in the second inflation/deflation process, pulses with similar amplitudes can be easily averaged to reduce noise and therefore more robust features can be extracted. This may provide better data for pulse wave analysis. In some implementations, the pulse information from holding the applied pressure at the second pressure can be used to validate information obtained from the first pressure profile.

FIG. 10 shows a graph for a blood pressure measurement depicting a first pressure profile followed by a second pressure profile, where the second pressure profile inflates to a targeted pressure and is held at the targeted pressure; the targeted pressure, in this example, is the maximum amplitude pressure seen in the oscillometric data, which may correspond to the user's mean arterial pressure. The first pressure profile shows a substantially linear inflation profile with oscillometric data being recorded during inflation. An applied pressure in the first pressure profile exceeds a maximum amplitude pressure recorded from the oscillometric data. The maximum amplitude pressure corresponds to the pressure at which the largest amplitude pressure changes (reproduced below the first pressure profile). Pressure is released to deflate the blood pressure cuff to zero gauge pressure or approximately zero gauge pressure. A second inflation follows where the blood pressure cuff is inflated to reach the targeted pressure, where the targeted pressure corresponds to the maximum amplitude pressure determined from the oscillometric data in the first pressure profile. The pressure is held or maintained at the targeted pressure, which can be the user's mean arterial pressure. The pressure is held for a duration sufficient to produce pulse information in a second pressure profile. The second pressure profile is recorded and shows a substantially linear inflation profile with additional oscillometric data (referenced to as pulse information, in this example) being recorded when the pressure is held at the targeted pressure. In some embodiments, systolic blood pressure and diastolic blood pressure can be determined from the pulse information in the second pressure profile. Inflections, peaks, and other features from the additional oscillometric data or pulse information may be analyzed to extract more pulse features.

FIG. 11 shows a graph for a blood pressure measurement depicting a first pressure profile followed by a second pressure profile, where the second pressure profile deflates to a targeted pressure and is held at the targeted pressure. Similar to FIG. 10, the first pressure profile shows a substantially linear inflation profile with oscillometric data being recorded during inflation, where a pressure exceeds a maximum amplitude pressure recorded from the oscillometric data. Then the blood pressure cuff is deflated to reach a targeted pressure, where the targeted pressure corresponds to the maximum amplitude pressure determined from the oscillometric data in first pressure profile. The pressure is held or maintained at the targeted pressure, which can be the user's mean arterial pressure. The pressure is held for a duration sufficient to produce pulse information in a second pressure profile. The second pressure profile is recorded, where additional oscillometric data (referenced to as pulse information, in this example) in the second pressure profile is recorded when the pressure is held at the targeted pressure.

Position Detection of the Blood Pressure Cuff

The blood pressure cuff of the present disclosure may be equipped with one or more sensors to determine a relative position of the blood pressure cuff with respect to a user's heart and/or, in some instances, an angular orientation of user's appendage that is inserted into the cuff relative to the earth's gravitational field. The one or more sensors may be coupled with a controller or control unit to receive data from the one or more sensors and determine whether the blood pressure cuff is properly positioned. In order to obtain an accurate blood pressure measurement for a finger blood pressure cuff, a height of a finger to which the finger blood pressure cuff is attached is preferably located to be about the same height the user's heart. That way, the blood pressure measurement can factor out hydrostatic pressure that can otherwise lead to an inaccurate measurement.

In some implementations of the present disclosure, the blood pressure cuff may include one or more accelerometers. The one or more accelerometers may be used to estimate the relative position of the blood pressure cuff with respect to a user's heart and also to determine whether the blood pressure cuff is in motion or not. When a user's finger is positioned within a finger blood pressure cuff, an angle of the finger blood pressure cuff may be determined to assist in determining whether the user is holding the finger blood pressure cuff in the correct position. In some implementations, the one or more accelerometers are configured to measure an angle of the blood pressure cuff with respect to gravity. In some implementations, the one or more accelerometers may be used to measure inclinations, including a roll angle and a pitch angle, about axes that are orthogonal or substantially orthogonal to a vertical axis. The roll angle and the pitch angle may be within a threshold to assist in determining that the blood pressure cuff is positioned proximate to the user's heart. For example, each of the pitch angle and the roll angle may be between about 0 degrees and about 30 degrees when the finger blood pressure cuff is positioned at approximately the same elevation as the user's heart. The one or more accelerometers may be configured to measure acceleration in at least two orthogonal directions or three orthogonal directions. Acceleration outputs ($A_x$, $A_y$, and $A_z$) may be generated and provided to the controller, and the controller may use the acceleration outputs to determine an inclination of the finger blood pressure cuff, where the inclination may be associated with the user's position of the hand/finger at an elevation of the user's heart.

Figure 13:
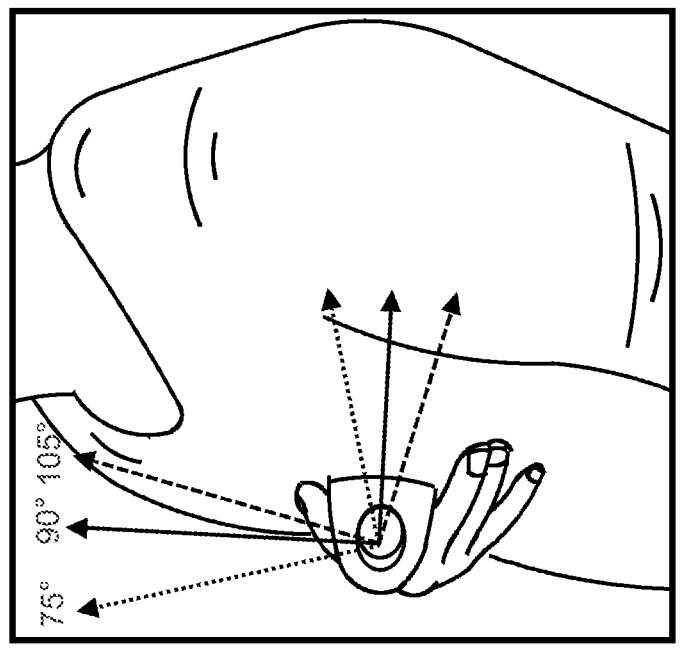
FIGS. 12 and 13 show photographs of an example finger blood pressure cuff as it may be worn during a measurement with a user placing their hand on their chest at an angle.
Figure 12:
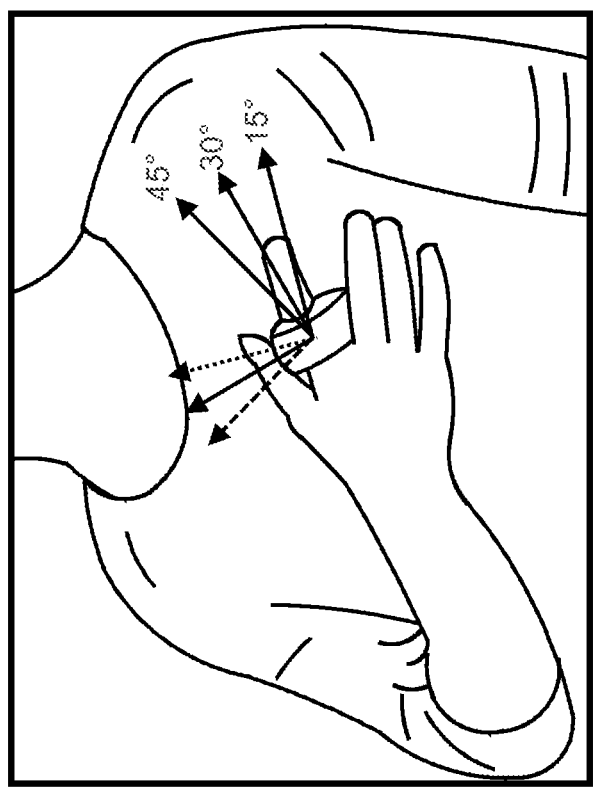

FIGS. 12 and 13, for example, are photographs showing an example finger blood pressure cuff depicted in earlier Figures as it may be worn during a measurement, with the user placing their hand on their chest at an angle. This positioning generally results in the finger blood pressure cuff being at the same altitude as the person's heart. In some implementations, a tri-axial accelerometer may be used to evaluate orientation of the finger blood pressure cuff relative to the earth's gravitational field. The finger blood pressure cuff may check for angular orientation with respect to all three axes to determine whether the user's forearm (or, more precisely, the user's finger) is at an angle between 15° and 45° from a horizontal axis, and whether a base (or other predefined reference surface) of the finger blood pressure cuff is approximately parallel to a vertical axis. For example, determining whether the base is approximately parallel to the vertical axis can mean that the base is parallel to a plane that is between about 75° and about 105° C. from the vertical axis. In other words, the finger blood pressure cuff may view a range of angular orientations as being within acceptable bounds for such a determination as being approximately the same altitude as the user's heart, e.g., with the bottom or base of the apparatus within ±15° of vertical and the centerline of the apparatus (the centerline of the bladder/opening) at 30°±15° of horizontal. When such a determination is made by the accelerometer, the finger blood pressure cuff may activate the pump to inflate an inflatable bladder to initiate a process for obtaining a blood pressure measurement.

In addition or in the alternative, the blood pressure cuff may include one or more altimeters. The one or more altimeters may detect changes in altitude and may be configured to determine an elevation of the blood pressure cuff with respect to a user's heart. In some implementations, the one or more altimeters may measure the change in elevation in response to changes in angle of the blood pressure cuff, and may be used to instruct the user to reach the correct level (e.g., "lower your hand by 2 inches").

In addition or in the alternative, the blood pressure cuff may include one or more auscultation sensors to acoustically determine a location of the user's heart. In some implementations, the one or more auscultation sensors include a microphone to listen for a user's heartbeat and determine proximity to the user's heart accordingly. Thus, the one or more auscultation sensors may be used as one or more proximity sensors to determine whether the blood pressure cuff is positioned proximate to the user's heart.

In addition or in the alternative, the blood pressure cuff may include one or more optical sensors for determining that the user's finger is positioned within a hole of the blood pressure cuff. As discussed above, the material of the inflatable bladder may be transparent or substantially transparent to certain wavelengths of light. The one or more optical sensors may be incorporated within the finger blood pressure cuff or, more specifically, within the inflatable bladder. The one or more optical sensors may be configured to detect whether a user's finger has been inserted through the hole of the blood pressure cuff. In some implementations, the one or more optical sensors may include one or more photoplethysmographic (PPG) sensors. The one or more PPG sensors may be used to determine at least one of a user's heart rate, respiration rate, skin condition, or other physiological metrics.

In some implementations, the one or more accelerometers or other motion sensors may be used to determine whether the blood pressure cuff is in motion or not. The blood pressure cuff may be configured to not initiate a blood pressure measurement and inflate the elastic bladder of the finger blood pressure cuff while the finger blood pressure cuff is in motion. When the blood pressure cuff is properly positioned at the elevation of the user's heart and measured motion is low enough for a sufficient duration, a blood pressure measurement may be initiated. The controller may automatically initiate inflation of the inflatable bladder when the one or more motion sensors (e.g., one or more accelerometers) determine that the finger blood pressure cuff is positioned within a threshold elevation of the user's heart or positioned proximate to the user's heart for a sufficient duration. A sufficient duration may be between about 0.5 seconds and about 5 seconds or between about 1 second and about 3 seconds. For example, a threshold elevation may be within ±2 inches of the user's heart, or within a targeted angular orientation as described above.

In some implementations, the controller may be configured to turn off the blood pressure cuff or enter a power-saving mode when the blood pressure cuff is motionless or stationary for a threshold duration and the one or more motion sensors determine that the device is not positioned within the threshold elevation of the user's heart. The controller may automatically turn off the blood pressure cuff or enter a power-saving mode when the one or more motion sensors determine that the finger blood pressure cuff has been motionless for a threshold duration, where a threshold duration may be between about 5 seconds and about 1 minute or between about 10 seconds and about 30 seconds. In some implementations, the sufficient duration and/or threshold duration may be defined by a user. In some implementations, the blood pressure cuff may be configured to turn off or enter a power-saving mode when the finger blood pressure cuff is oriented in a manner with respect to gravity to indicate that the finger blood pressure cuff is not in use. For example, the controller may automatically turn off the finger blood pressure cuff or enter a power-saving mode when the one or more motion sensors determine that a substrate or flat surface (e.g. base) of the blood pressure cuff is oriented orthogonally with respect to gravity.

Figure 14:
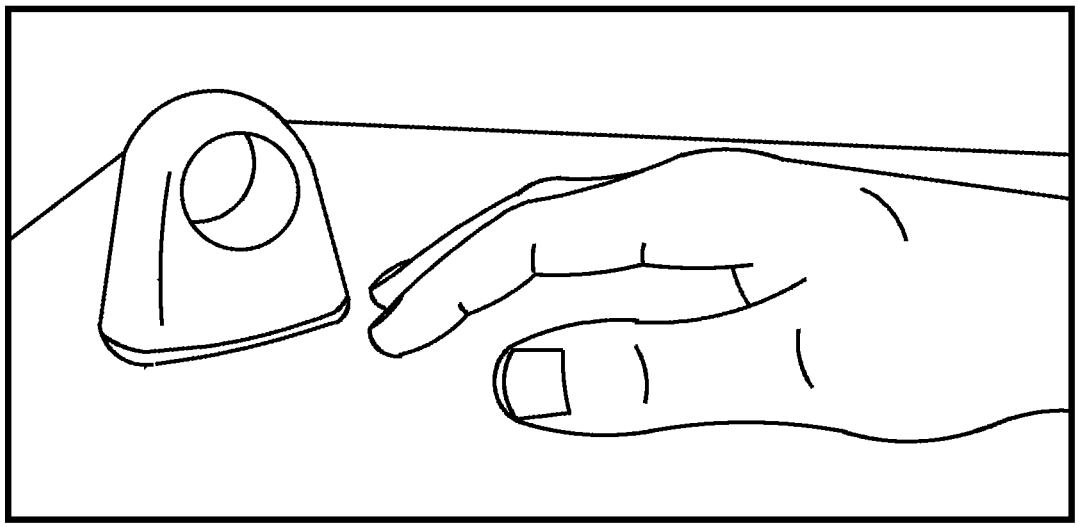
FIGS. 14 and 15 show photographs of an example finger blood pressure cuff resting on a surface and with a finger inserted through an opening of the finger blood pressure cuff to take a blood pressure measurement.
Figure 15:
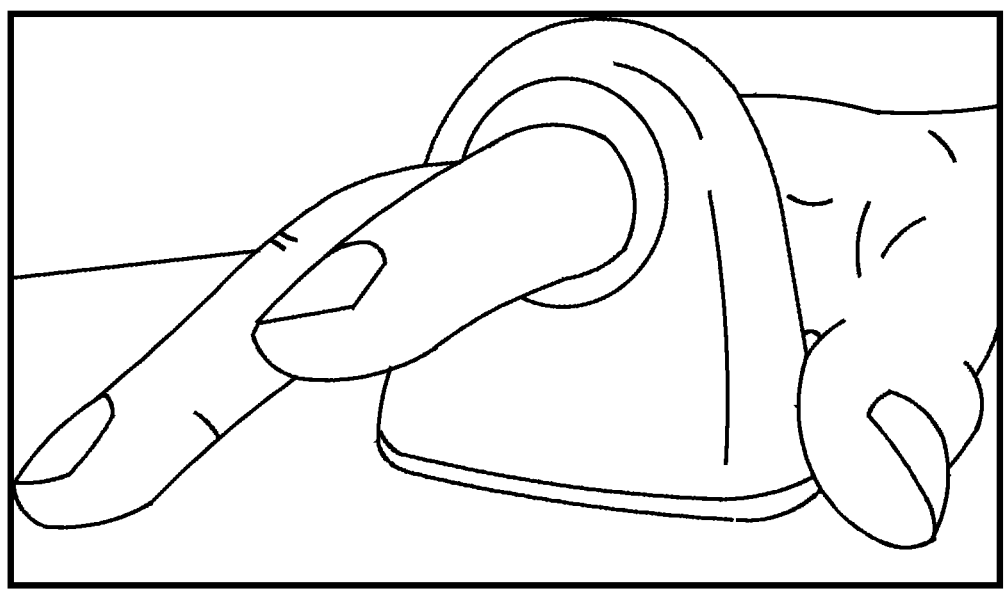

FIGS. 14 and 15 show photographs of an example finger blood pressure cuff resting on a surface and with a finger inserted through an opening of the finger blood pressure cuff to take a blood pressure measurement. When the finger blood pressure cuff is resting on the surface as shown in FIG. 14, a pump is not activated to inflate an inflatable bladder. In some implementations, the finger blood pressure cuff may be configured to turn off or enter a power-saving mode when resting on the surface for a long enough duration. Regardless of whether the finger blood pressure cuff is resting on a surface or not, a user's finger may be inserted through an opening of the finger blood pressure cuff as shown in FIG. 15. In some implementations, a pump is activated to cause inflation of an inflatable bladder to make contact around the user's finger. The finger blood pressure cuff may be configured to take a blood pressure measurement when the user's finger is inserted through the opening and the inflatable bladder is inflated to contact the user's finger. While the finger blood pressure cuff can be used to take a blood pressure measurement with the finger blood pressure cuff resting on a surface, it will be understood that the finger blood pressure cuff can be used to take a blood pressure measurement when the finger blood pressure cuff is not resting on a surface. In some implementations, more accurate blood pressure measurements can be taken when the finger blood pressure cuff is positioned at the same or substantially the same elevation as the user's heat or positioned proximate to the user's heart.

In some implementations of the present disclosure, the blood pressure cuff may include one or more proximity sensors. The one or more proximity sensors may be configured to determine whether the blood pressure cuff is proximate to a user's heart or not. In addition or in the alternative, the one or more proximity sensors may be configured to determine whether the user's appendage (e.g., user's finger) is properly positioned in the blood pressure cuff. Examples of proximity sensors may include capacitive, optical, and photoelectric sensors. The one or more proximity sensors may be used to detect the presence of a user's chest, skin, body, or finger. In some implementations, the blood pressure cuff further includes one or more motion sensors to determine whether the device is in motion or stationary. In some implementations, the blood pressure cuff further includes a controller configured to initiate inflation of the inflatable bladder using a pump when the one or more proximity sensors determine that the blood pressure cuff is positioned proximate to the user's heart and when the one or more motion sensors determine that the device is stationary for a sufficient duration.

In some implementations, the one or more proximity sensors include one or more auscultation sensors configured to acoustically determine proximity to the user's heart. The one or more auscultation sensors function as a stethoscope to listen for a user's heartbeat and determine proximity to the user's heart. The one or more auscultation sensors can include a microphone that acts as the proximity sensor to acoustically determine a location of the user's heart, thereby assisting in proper positioning of the blood pressure cuff prior to making a blood pressure measurement.

In some implementations of the present disclosure, the blood pressure cuff may further include one or more feedback devices. The one or more feedback devices may be configured to communicate positioning of the blood pressure cuff relative to the user's heart and/or positioning of the user's finger relative to the opening of the blood pressure cuff. Feedback from the one or more feedback devices may include communicating to the user that a blood pressure measurement is occurring, that a blood pressure measurement is complete, that the elastic bladder is inflating, that the elastic bladder is deflating, whether the blood pressure cuff is properly positioned or not, whether the user's finger is properly positioned or not, information regarding physiological data associated with the user such as systolic pressure, diastolic pressure, mean arterial pressure, heart rate, respiratory rate, and blood pressure risk zone/information. The one or more feedback devices may include but is not limited to a speaker for audio feedback, light-emitting diodes (LED) for optical feedback, a display for visual feedback, and motor/vibramotor for haptic feedback. In some implementations, the one or more feedback devices may include a display to present visual feedback to the user. The display (e.g., screen) may display guidance, user, connectivity, biometric data, and/or blood pressure results to the user. In some implementations, the one or more feedback devices may include a speaker and/or microphone for audio control and guidance. In some implementations, the blood pressure cuff includes an interface for receiving any or all of the aforementioned feedback by way of one or more intermediary devices (from one device to another), such as from a smartphone, a wearable device, computer, or remote server. In some implementations, a remote device such as a smartphone, wearable device, computer, or remote server may provide any or all of the aforementioned feedback directly to the user.

Other Embodiments

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

As used herein, terms such as "about," "approximately," "nominally," and the like with respect to numerical values or relationships, e.g., perpendicularity or parallelism, are to be understood to include, unless otherwise indicated, the value or relationship indicated ±10% of that value or relationship (e.g., for approximately parallel, the value may be 90°±9°).

The present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

What is claimed is:

1. A device for estimating a user's blood pressure, the device comprising:
    a rigid housing having a hole sized to receive a human finger, the rigid housing including a base having a flat surface;
    an inflatable bladder defining, at least in part, a pressurizable volume, wherein the inflatable bladder is disposed about an inward-facing surface of the hole of the rigid housing;
    a pump in fluidic communication with the inflatable bladder and configured to pressurize the pressurizable volume and cause the inflatable bladder to inflate and contact a user's finger when the pump is activated;
    a pressure sensor in fluidic communication with the inflatable bladder and configured to produce pressure data indicative of pressure within the pressurizable volume as a function of time;
    one or more accelerometers in the housing, wherein the one or more accelerometers are configured to determine relative positioning of the device with respect to a user's heart by measuring inclinations about axes that are orthogonal to a vertical axis, the inclinations including a roll angle and a pitch angle;
    one or more optical sensors disposed within the pressurizable volume, the one or more optical sensors configured to detect whether the user's finger is positioned within the hole of the housing; and
    a controller configured to initiate inflation of the inflatable bladder using the pump in response to the flat surface of the base being substantially parallel to the vertical axis or the one or more accelerometers determining that the device is positioned within a threshold elevation with respect to the user's heart and that the device is stationary for a threshold duration.

2. The device of claim 1, wherein when the controller is configured to initiate inflation of the inflatable bladder using the pump in response to the one or more accelerometers determining that the device is positioned within the threshold elevation with respect to the user's heart and that the device is stationary for the threshold duration, the controller is further configured to turn off the device or enter a power-saving mode in response to the one or more accelerometers determining that the device is not positioned within the threshold elevation with respect to the user's heart and is stationary for a sufficient duration between about 0.5 seconds and about 5 seconds.

3. The device of claim 1, wherein each of the roll angle and the pitch angle is between about 0 degrees and about 30 degrees when the device is determined to be at approximately the same elevation as the user's heart.

4. The device of claim 1, further comprising:
    one or more auscultation sensors configured to acoustically determine a location of the user's heart.

5. The device of claim 1, further comprising:
    one or more proximity sensors, wherein the one or more proximity sensors are configured to determine that the device is positioned proximate to the user's heart.

6. The device of claim 5, wherein the one or more proximity sensors include one or both of an auscultation sensor and a microphone configured to acoustically determine that the rigid housing of the device is in proximity of the user's heart.

7. The device of claim 1, wherein the base of the rigid housing is within 90°±15° of the vertical axis and a centerline of the hole through which the user's finger passes through is at 30°±15° of a horizontal axis when the device is determined to be at approximately the same elevation as the user's heart.

8. The device of claim 1, wherein the one or more optical sensors comprise at least one photoplethysmographic (PPG) sensor.

9. The device of claim 8, wherein the at least one PPG sensor is configured to determine at least one of a heart rate, a respiration rate, or a skin condition.

10. The device of claim 1, wherein the pressurizable volume includes a plurality of lobes.

11. The device of claim 1, wherein the controller is further configured to communicate a notification indicative of a position of the user's finger relative to the hole of the rigid housing.

12. The device of claim 11, wherein the controller is further configured to communicate a notification indicative of a position of the device relative to the user's heart.

13. The device of claim 11, wherein the notification comprises an audible notification or a visual notification.

14. The device of claim 1, wherein the inflatable bladder is transparent.

15. The device of claim 1, wherein in response to the one or more optical sensors detecting the user's finger is positioned within the hole of the housing, the controller is configured to further inflate the inflatable bladder to increase a pressure of the pressurizable volume.

* * * * *